(12) United States Patent
Momose et al.

(10) Patent No.: US 7,638,298 B2
(45) Date of Patent: Dec. 29, 2009

(54) METHOD FOR DETECTING MUTATION AND A METHOD FOR INDUCING MUTATION

(75) Inventors: Masaki Momose, Tochigi (JP); Naoyuki Umemoto, Tochigi (JP); Hiroshi Okawa, Tokyo (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 299 days.

(21) Appl. No.: 10/571,779

(22) PCT Filed: Sep. 16, 2004

(86) PCT No.: PCT/JP2004/014007

§ 371 (c)(1),
(2), (4) Date: Mar. 15, 2006

(87) PCT Pub. No.: WO2005/026363

PCT Pub. Date: Mar. 24, 2005

(65) Prior Publication Data

US 2007/0009896 A1    Jan. 11, 2007

(30) Foreign Application Priority Data

Sep. 16, 2003    (JP) ............................. 2003-323428

(51) Int. Cl.
*C12N 15/29* (2006.01)
*C12N 15/00* (2006.01)
*C12N 15/63* (2006.01)
*C12N 5/14* (2006.01)

(52) U.S. Cl. ...................... 435/69.1; 435/473; 435/410; 435/440; 536/23.1

(58) Field of Classification Search ........................ None
See application file for complete search history.

(56) References Cited

U.S. PATENT DOCUMENTS 7,132,587 B2 * 11/2006 Kikuchi et al. .............. 800/276

FOREIGN PATENT DOCUMENTS

JP    2003-093074 A    4/2003

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
D.R. Lisch et al., "Mutator transposase is widespread in the grasses", Plant. Physiol., 2001, vol. 125, No. 3, pp. 1293-1303.
X. Zhang et al., "P instability factor: an active maize transposon system associated with the amplification of Tourist-like MITEs and a new superfamily of transposases", Proc. Natl. Acad. Sci. USA, 2001, vol. 98, No. 22, pp. 12572-12577.

* cited by examiner

*Primary Examiner*—Maria Marvich
(74) *Attorney, Agent, or Firm*—Stephen A. Bent; Foley & Lardner LLP

(57) ABSTRACT

A novel plant transposon that induces bud mutation, transposase thereof, and a method for efficiently inducing bud mutation by improvement in the transposition efficiency are provided. A novel transposon having terminal inverted repeat sequences (SEQ ID NO: 1 and SEQ ID NO: 2) shown below has been isolated for the first time from carnation (*Dianthus caryophyllus*) and the nucleotide sequence thereof has been determined. The transposon has contained a gene encoding the transposase in its sequence. The transposon induces bud mutation when it is inserted into a gene. The transposition frequency is elevated due to environmental stress. TAGAGCTGGCAAA---TTTGCCAGCTCTA (SEQ ID NOS 1 & 2, respectively in order of appearance).

5 Claims, 9 Drawing Sheets

Fig. 1

| Name | Biological species (genus and species) | Cluster | Sequence |
|---|---|---|---|
| Transposon of the present invention | D. caryophyllus | | TAGAGCTGGCAAA |
| Ac | Z. mays | Ac | TAGGGATGAAA |
| Tam3 | A. majus | Ac | TAAAGATGTGAA |
| Slide | N. tabacum | Ac | TAATGCTG |
| | A. thaliana | Ac | CAGAAAAA |
| | A. thaliana | Ac | TAGCCCTG |
| | A. thaliana | Ac | TAGGGGTGTCAAAA |
| | A. thaliana | Ac | GAAACATGA |
| | A. thaliana | Ac | TGAAGATGC |
| | A. thaliana | Ac | TAGGGATGTT |
| | A. thaliana | Ac | TAGAAGTGTCAA |
| | A. thaliana | Ac | TAGGGGTGTCAA |
| | A. thaliana | Ac | TAGGGGTGTCAAAA |
| | A. thaliana | Ac | AAGTTATA |
| | A. thaliana | Ac | AAGTTATA |

Fig. 2-1

```
>gi|100489|pir||S13518     transposase Tam3 - garden snapdragon transposon Tam3
 gi|16064|emb|CAA38906.1|     Tam3-transposase [Antirrhinum majus]
 gi|3219237|dbj|BAA28817.1|    transposase [Antirrhinum majus]
 gi|3219239|dbj|BAA28818.1|    transposase [Antirrhinum majus]
 gi|3219241|dbj|BAA28819.1|    transposase [Antirrhinum majus]
 gi|3219244|dbj|BAA28820.1|    transposase [Antirrhinum majus]
 gi|3219249|dbj|BAA28821.1|    transposase [Antirrhinum majus]
 gi|3219251|dbj|BAA28822.1|    transposase [Antirrhinum majus]
 gi|3219256|dbj|BAA28823.1|    transposase [Antirrhinum majus]
 gi|3219259|dbj|BAA28824.1|    transposase [Antirrhinum majus]
 gi|12060255|dbj|BAB20481.1|    Tam3 transposase [Antirrhinum majus]
          Length = 749

Score =  289 bits (740), Expect = 1e-76
 Identities = 183/624 (29%), Positives = 318/624 (50%), Gaps = 39/624 (6%)

Query  177  RKNSSVAWPHYILTTDKKKAKCRYCNTIYTAKSQNGTGHLIRHITKKCTAMPQAGQSTMD  236
             +  + W + T   A+C  C TY+ K+  GTG L RH+T K            MD
Sbjct  125  KTKKATVWKWFSKVTGSNWAQCLLCPTRYSHKTGCGTGTLTRHLTAK------HKNRDMD  178

Query  237  --DFLTKPNAP-EQYKYDYDECSAELSKMIIQTEEPFLLAERNAFNRYVKKN-QPEHKPT  292
              D  +P+   ++YD +    L++ I+Q E PF A+   F  +++K Q + K
Sbjct  179  APDMQRQPDGTMAPWRYDQNYMRICLAQFIVQNELPFSFAQNELFENFLQKAVQCKFKKI  238

Query  293  GRRRVRSNAMQQYCTLKHKLIADFENMSCKFNLTADVWDSGVDYHYLCITAHWVDREWNL  352
              R    + ++QY     L  +F+N + +  +LT+D+W     YH+ CITAHW+D++W +
Sbjct  239  SRATCFRDGVKQYEKEIIVLRNEFKNFNGRISLTSDLWQGSGSYHFSCITAHWIDKDWIM  298

Query  353  QKRIISFSKLEFPHNAINMHNIIMASINEYNIKSKILTVTFDNATSMTAVANMLKNSLES  412
             +KRII F++L+ PHN  + +  M+S+N + IK KI++++ DNA++       LK ++ +
Sbjct  299  RKRIIEFAQLDSPHNGDCIRDATMSSLNYWGIKDKIMSISLDNASNNVNAIKSLKPAM-N  357

Query  413  VLLNGDLLHVRCACHVLNLCVRDGLEGLKQYHSTFKHVVLHLNSNKSRRQEWRNYCKSVG  472
             ++L G L HVRC CH+L+LCV+DGL   L Q      + +H+N   R Q    C++ G
Sbjct  358  LILGGQLFHVRCICHILHLCVKDGLSVLIQSIDRIRVCLSHINRYPPRVQAFNTVCETHG  417

Query  473  VKYRKFPMENNTRWNSMYIMLSACIEYKQPLTAFWNGIFPDSPILENHWNNMEMYVDFLC  532
              +  +  ++   RWN+ Y ML     Y +P+T F +     + IL + WN  ++ V +L
Sbjct  418  MPIKHIYLDVPHRWNATYRMLIEAKPYSEPITFFCHRSLGPNSILADDWNICDILVPYLV  477

Query  533  AFMDATKSFSHVYKTTAPYFLGNIIPIAELFQKYRAQQSYLGFLPKMEEKFLKYWTDIPY  592
                F + TK  S  Y T+   L ++ +  LF ++R     +  + +ME+K++KY+  +P
Sbjct  478  YFEEFTKIMSSCYTPTSNIMLLYMVSVVRLFHQHRNHATLKNIIKEMEKKWVKYYKKVPN  537

Query  593  VYVFAVILDPRWKFDGAISLVTIYKQLMNIDFDPDLYKDEIRQAFFNVYNHYESRIGPST  652
             V + +  LDPR + G + L+  Y  +N ++   ++ I Q    +++Y+ Y      PST
Sbjct  538  VCILSSCLDPRVRLIGTLELLEKYHSALNNVYNGNEERNRILQLLYSLYDMY----APST  593
```

Fig.2-2

```
Query: 653 RPPXXXXXXXXXXXXXXXXXXXXTLNKLKG----LVSQLRPDVAQSTSTTSDLAEYHMYINYD 708
                                 N  +G     +  +L  +   +   +   +  E H+++
Sbjct: 594 ---------------DMDESPTNASRGSGFSIFDELLSNQQSNQPSVGNYTEIHLFVQKP 638

Query: 709 YLRSFTDEEANVLDLLLWWKGQRRQLPVMSAMAQDFLSIQVSSVASERAFSASKRVLDEK 768
              +   D      D+L WW+      PV++ +A+D LS Q+S+VASERAFSA  RVL +
```

Fig. 3-1

```
Query:  ccttgtttttgcaccttatggacctaaatggcgcatgctt
        ||||||||||||||||||||||||||||||||||||||||
Sbjct:  ccttgtttttgcaccttatggacctaaatggcgcatgctt Query:  aggaaaatttgttccttacacatgttttcttctaaggctttggacgattttagacttgt
        |||||||||||||||||||||||||||||||||||||||||||||||||||||||||||
Sbjct:  aggaaaatttgttccttacacatgttttcttctaaggctttggacgattttagacttgt Query:  ccgtcaggaagaagtatctatactggtaaacgcgatagcaaaagcaggaacaaagccagt
        |||||||||||||||||||||||||||||*|||||||||||||||||||||||||||||
Sbjct:  ccgtcaggaagaagtatctatactggtaaatgcgatagcaaaagcaggaacaaagccagt Query:  acaactaggacaactactactcaacgtgtgcaccacaaatgccttatcgagggtgatgct
        ||||||||||***|||||||||||||||||||||||||||||||||||||||||||||
Sbjct:  acaactaggaca---actactcaacgtgtgcaccacaaatgccttatcgagggtgatgct Query:  agggaagcgagttctcggtgatggcacagggaaaagcgacccaaaagccgaggaatttaa
        ||||||||||||||||||||||||||||||||||||||||||||||||||||||||||||
Sbjct:  agggaagcgagttctcggtgatggcacagggaaaagcgacccaaaagccgaggaatttaa Query:  ggacatggtgctggagttaatggttctcaccggagtttttaacattggcgattttgtacc
        ||||||||||||||||||||||||||||||||||||||||||||||||||||||||||||
Sbjct:  ggacatggtgctggagttaatggttctcaccggagtttttaacattggcgattttgtacc Query:  ggcattggaatgtctagacttacaaggtgttgcatctaaaatgaagaaattacataaaag
        ||||||||||||||||||||||||||||||||||||||||||||||||||||||||||||
Sbjct:  ggcattggaatgtctagacttacaaggtgttgcatctaaaatgaagaaattacataaaag Query:  acttgataattttatgagtaacattttggaggaacacaagagtgttgcacatcaacaaaa
        ||||||||||||||||||||||||||||||||||||||||||||||||||||||||||||
Sbjct:  acttgataattttatgagtaacattttggaggaacacaagagtgttgcacatcaacaaaa Query:  tggtggagatttgctaagcactttgatatctttgaaggataattgtgatggtgaaggtgg
        ||||||||||||||||||*|||||||||||||||||||||||||||||||||||||||||
Sbjct:  tggtggagatttgctaagcattttgatatctttgaaggataattgtgatggtgaaggtgg Query:  caagtttagtgacacagaaattaaggccttgctattggatttatttacagctggaacaga
        |||||||||*||||||||||||||||||||||||||||||||||||||||||||||||||
Sbjct:  caagtttagtgccacagaaattaaggccttgctattggatttatttacagctggaacaga Query:  cacatcatctagtacaactgaatgggccatagccgaactaattcgccatccaaaaatctt
        ||||||||||||||||||||||||||||||||||||||||||||||||||||||||||||
Sbjct:  cacatcatctagtacaactgaatgggccatagccgaactaattcgccatccaaaaatctt Query:  agcccaagttcaacaagaaatggactcagtcgtgggccgagaccgactcatagccgaagc
        ||||||||||||||||||||||||||||||||||||||||||||||||||||||||||||
Sbjct:  agcccaagttcaacaagaaatggactcagtcgtgggccgagaccgactcatagccgaagc
```

Fig. 3-2

```
Query:  tgacataccgaacctaacctacttccaagccgtaatcaaagaggttttccgacttcaccc
        ||||||||||||||||||||||||||||||||||||||||||||||||||||||||||||
Sbjct:  tgacataccgaacctaacctacttccaagccgtaatcaaagaggttttccgacttcaccc Query:  gtccacccogctttccctaccacgggtcgcaaacgaatcgtgtgaaataaacgggtacca
        |||||||||||||||||||||||||||||||||||||||*||||||||||||||||||||
Sbjct:  gtccacccogctttccctaccacgggtcgcaaacgaatcgtgcgaaataaacgggtacca Query:  cattcccaaaaacaccactttattggtg
        |||||||||||||||||||||||||||*
Sbjct:  cattcccaaaaacaccactttattggta
```

METHOD FOR DETECTING MUTATION AND A METHOD FOR INDUCING MUTATION

TECHNICAL FIELD

The present invention relates to a method for detecting mutation, a method for inducing mutation, a method for stabilizing mutation, a method for identifying a mutated gene, and selection of a mutant wherein gene expression has been suppressed. These are achieved by using a novel transposon that induces plant bud mutation, its transposase and a nucleotide sequence encoding the transposase.

BACKGROUND ART

Mutation is important for crop breeding and molecular genetic studies. Naturally arising bud mutation and artificial mutation are used. "Bud mutation" in the present invention indicates mutation that occurs in some somatic cells of a plant at the gene level. "Bud mutant" in the present invention indicates such a mutant. In the case of vegetatively propagated crops, such as flowers and ornamental plants and orchards, bud mutation that takes place without crossing provides genetic mutation important for developing varieties. However, the cause of the molecular mechanism of mutation due to bud mutation is unknown. Bud mutation depends on natural occurrence. Furthermore, natural mutation is thought to take place at a probability of only approximately one to one million. To increase such efficiency, radiation irradiation and techniques using chemical substances having mutagenicity have been used to induce mutation. When increase of a mutation occurrence rate is attempted, undesired mutation is introduced in addition to desired mutation. Thus, many cases result in obtainment of very poor phenotypes together with a target phenotype. This requires a search for a target mutant from among a mutant population comprising numerous plants and also results in low efficiency.

A transposon (also referred to as a transposable element) is a mobile genetic element that is broadly found among biological species ranging from prokaryotes to eukaryotes and that undergoes transposition on the genome. In plants, such transposon has been discovered in *Arabidopsis thaliana, Brassica campestris*, and the like [JP Patent Publication (Kokai) No. 2003-93074 A]. Furthermore, a transposon that controls the expression of an anthocyanin biosynthetic gene in maize (*Zea mays*) grains, snapdragon petals (*Antirrhinum majus*) [PROTEIN, NUCLEIC ACID AND ENZYME 37 1047-1059 (1992)], Japanese morning glory petals (*Pharbitis nil*) [Proc. Natl. Acad. Sci. U.S.A. 97: 7016-7023 (2000)], petunia petals (*Petunia hybrida*) [The Plant Journal 13: 39-50 (1998)], carnation petals (*Dianthus caryophyllus*), or the like is known well.

For example, in the case of a carnation variety having white petals with red spots, a transposon has been inserted within a dihydroflavonol-4-reductase (an anthocyanin biosynthetic enzyme hereinafter referred to as DFR) gene. The DFR gene is necessary for red pigment synthesis. When a transposon has been inserted, the DFR gene does not function, so that white flower color will be developed. However, it has been elucidated that the DFR gene function can be recovered and a pattern of red spots can be generated by excision of such inserted transposon at the time of petal formation [Plant Cell Physiology. 43: 578-585 (2002)]. Regarding the above-mentioned case of developing mutation sectors due to excision of a transposon in some cells within an individual plant, the involvement of a transposon has been elucidated in maize, snapdragon, Japanese morning glory, petunia, and the like via molecular genetics.

Furthermore, it has also been revealed that mutation due to a transposon is inherited via reproductive cells to progeny. In this case, the transposition of a transposon has taken place during the period of reproductive cell formation. Mutants resulting from such transposition can be obtained in the progeny. By the use of this phenomenon, a gene isolation technique has been developed that involves introducing a known transposon by gene transfer or the like and then analyzing mutants obtained in the progeny using the introduced transposon as a landmark. This technique is called transposon tagging [The Plant Journal 7: 677-685 (1995)].

As described above, the use of a transposon as a mutagen has been attempted. However, current techniques are insufficient for obtaining mutation due to the insertion of a transposon into a gene in buds. With such current techniques, mutants are obtained at best mainly via crossing or hybridization. Such case where the transposition of a transposon takes place among some cells composing an individual plant is known. For example, a case of bud mutation induced by a retrotransposon has been reported [Science 304: 982 (2004)]. However, no cases have been reported where such bud mutation that can be fixed by vegetative propagation is induced by a transposon other than retrotransposon.

Patent document 1 JP Patent Publication (Kokai) No. 2003-93074 A

Non patent document 1 PROTEIN, NUCLEIC ACID AND ENZYME 37 1047-1059 (1992)

Non patent document 2 Proc. Natl. Acad. Sci. U.S.A. 97: 7016-7023 (2000)

Non patent document 3 The Plant Journal 13: 39-50 (1998)

Non patent document 4 Plant Cell Physiology. 43: 578-585 (2002)

Non patent document 5 The Plant Journal 7: 677-685 (1995)

Non patent document 6 Science 304: 982 (2004)

DISCLOSURE OF THE INVENTION

Bud mutants have been conventionally obtained by the use of natural mutation characterized by very low occurrence frequency or artificial mutation induced by radiation or a chemical substance that results in undesired mutation in addition to target mutation. Such techniques require the handling of numerous plants and selection of a target mutant from among such numerous plants. Thus, efficiency has been very low. Moreover, much labor is required for specifying a mutated gene in mutants obtained by such conventional methods. To solve these problems, objects of the present invention are to provide novel plant transposons that induce bud mutation, to provide a method for detecting the presence or the absence of such novel transposons, to provide a method for detecting the excision or the lack of excision of such novel transposons, and to provide a technique for inducing bud mutation using such novel transposons as a mutagen.

An ideal mutation method is that bud mutants can be efficiently obtained with the mutation of a small number of genes per cell. Such method can be developed by artificially promoting transposition of a transposon as a mutagen. Furthermore, causative gene isolation is facilitated because of the presence of such transposon as a landmark in a causative gene as described above.

As a result of intensive studies to solve the above problems, the present inventors have discovered the following knowledge using: carnation clone 95SP (Mrs. Purple, registered with variety registration No. 7291 under the Seed and Seedlings Law of Japan, Kirin Beer Kabushiki Kaisha) developing a purple flower color; a bud mutant thereof that is carnation clones 97SPi (Mrs. Pink Rosario, registered with variety registration No. 8976 under the Seed and Seedlings Law of Japan, Kirin Beer Kabushiki Kaisha.) developing a pink flower color; 97SE (Mrs. Elegant, registered with variety registration No. 9247 under the Seed and Seedlings Law of Japan, Kirin Beer Kabushiki Kaisha.) developing a dark red flower color; carnation variety Kaly (BARBERET & BLANC, S. A.); *Dianthus chinensis; Dianthus barbatus*; carnation clone 99SP4 developing a pink flower color; and carnation clone 99SP5 developing a pink flower color.

Specifically, DNA that is absent in carnation clone 95SP has been inserted in a genomic gene of carnation clone 97SPi encoding flavonoid 3' hydroxylase, which is an enzyme involved in anthocyanin biosynthesis. The nucleotide sequence inserted therein is provided with typical characteristics of a transposon. That is, the nucleotide sequence has the inverted repeat sequences each consisting of 13 nucleotides shown in SEQ ID NO: 1 and SEQ ID NO: 2, respectively, and being separately present on one end and on the other end. Nucleotide sequences each consisting of 8 nucleotides, being identical, and being oriented in the same direction are separately present on one side and on the other side of the position where the insertion sequence is present. Furthermore, the inverted repeat sequence is analogous to that of a transposon of maize AC (FIG. 1). However, no analogous properties have been observed concerning an internal nucleotide sequence of approximately 4 kb. An open reading frame is present in the nucleotide sequence. An amino acid sequence converted from the region of the nucleotide sequence shows homology with the amino acid sequence of transposase encoded by a transposon derived from snapdragon or the same derived from maize (FIG. 2). The expression of such transposase can be detected by return PCR (hereinafter referred to as return PCR).

Furthermore, in the case of petals of individual plants developing a purple flower color as a result of atavism from 97SPi, the inserted nucleotide sequence has been excised. Hence, it is clear that the nucleotide sequence retains transposition ability even after generation of 97SPi.

Moreover, a DNA nucleotide sequence has been obtained from 97SPi. The DNA nucleotide sequence has inverted repeat nucleotide sequences each consisting of 13 nucleotides shown in SEQ ID NO: 1 and SEQ ID NO: 2, respectively, and being separately present on one end and on the other end, but is thought to be a non-autonomous transposon lacking a transposase gene. This DNA sequence is also present in 95SP and in 97SE that is a mutant derived from 95SP. In the case of 97SE, the DNA sequence has been inserted in a new genome site that is absent in 95SP. Nucleotide sequences each consisting of 8 nucleotides, being identical, and being oriented in the same direction were separately present on one side and on the other side of the position where the sequence had been inserted. It was confirmed that the sequence is mobile because in the case of 97SE, the sequence had been inserted at a genome site differing from that in the case of 95SP.

According to the present invention, transposons that undergo transposition on the genome so as to induce bud mutation have been isolated and identified for the first time. Moreover, regarding transposons encoding transposase among the transposons of the present invention derived from the chromosomal DNA of the genus *Dianthus*, controlling the expression of the enzyme enables the control of transposition. Furthermore, the enzyme is also predicted to enable the control of transposition of those not encoding transposase among the transposons of the present invention. This is achieved by controlling the expression of transposase of such transposons encoding such transposase.

The transposons of the present invention have the property of inducing bud mutation. Accordingly, they have utility that enables efficient induction of bud mutation by the provision of specific environmental conditions, such as temperatures at which transposition is promoted, or by the artificial expression of transposase. It becomes possible to easily detect bud mutants by the use of the nucleotide sequence information concerning the transposons revealed by the present invention.

It also becomes possible to easily isolate a causative gene by the analysis of mutation induced by the transposons.

Furthermore, a mutant wherein gene expression has been suppressed can be obtained by inserting such a transposon into a gene without using genetic engineering techniques such as an antisense technique. In a case where obtainment of buds having disrupted genes is important, specifically, in the case of genetically heterogeneous plants or in the case of a gene involved in reproduction or seed development, bud mutation induced by a transposon is useful. Target gene-disrupted individual plants can be easily screened among mutants induced by the transposons. Moreover, it becomes possible to suppress gene expression without performing genetic engineering.

Furthermore, it becomes also possible to stabilize bud mutation by conversely refraining from exposing plants to the specific environmental conditions promoting transposition of the transposons (e.g., temperature) or by artificially suppressing transposase expression using techniques such as RNAi.

This description includes part or all of the contents as disclosed in the description and/or drawings of Japanese Patent Application No. 2003-323428, which is a priority document of the present application

BRIEF DESCRIPTION OF THE DRAWINGS

FIG. 1 shows homology comparison between the terminal inverted repeat sequence in the transposon of the present invention obtained from the plant (carnation clone 97SPi) and the same of various plants. In FIG. 1, "Cluster" refers to the type of transposon. Such cluster was prepared based on description given in Genetics 158: 949-957 2001. (SEQ ID NOS 1, and 29-35 are disclosed respectively in order of appearance.)

FIG. 2-1 shows homology comparison at the amino acid level between transposase in the plant (carnation clone 97SPi) used in the present invention and transposase of snapdragon transposon Tam3. In FIG. 2-1, those where notations such as R and Q are given between two sequences indicate that the relevant amino acids are identical each other. Those given with "+" indicate that the relevant amino acids are analogous to each other. For example, since L, I, V, and M are common among hydrophobic amino acids, such notations are given. Moreover, "Query" (SEQ ID NO: 36) indicates the amino acid sequence of transposase of the transposon of the present invention. "Sbjct" (SEQ ID NO: 37) indicates the amino acid sequence of transposase of the transposon Tam3 of snapdragon.

FIG. 2-2 is a continuation from FIG. 2-1.

FIG. 3-1 shows a comparison between the cDNA nucleotide sequence (Query) (SEQ ID NO: 38) of the 95SP flavonoid 3' hydroxylase (F3'H) gene and the cDNA sequence (Subject) (SEQ ID NO: 39) of the F3'H gene described in GenBank AX028819. "|" indicates homologous nucleotides and "*" indicates different nucleotides.

FIG. 3-2 is a continuation from FIG. 3-1.

[Lane description] 1: molecular weight marker (λHindIII); 2: 97SPi; 3: 95SP; 4-19: 97SPi; and 20-21: flower petals of 97SPi plants partially developing a purple flower color as a result of atavism.

Figure 5:
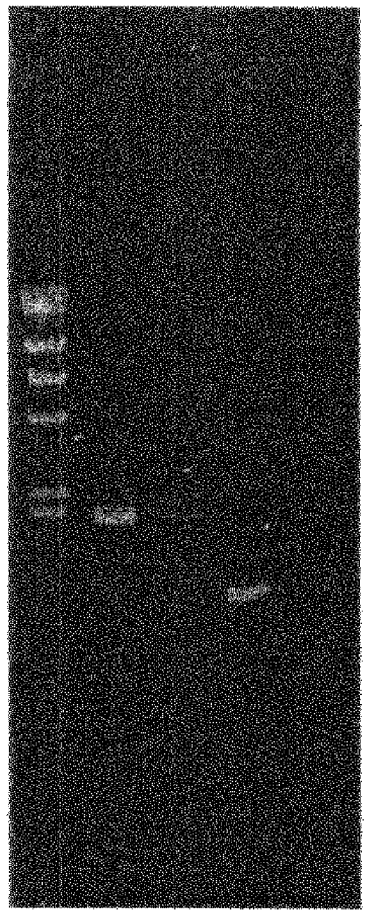

FIG. 5 shows confirmation of transcriptional expression of transposase in various carnation plants. cDNAs were prepared from clones 95SP and 97SPi. PCR (conditions: 95° C. for 2 minutes; 30 cycles of 95° C. for 30 seconds, 56° C. for 30 seconds, and 72° C. for 3 minutes; and 72° C. for 3 minutes) was performed (a) using primers CACTATGGATC-CTAATTCTCAAA (23 nucleotides: SEQ ID NO: 20) and GAGACTCATAGTGGTTATATACA (23 nucleotides: SEQ ID NO: 14). Furthermore, PCR was similarly performed (b) using primers TTCTTCACTTGAATTCGAACAAG (23 nucleotides: SEQ ID NO: 21) and CGCAAATACAC-TAAATTTATGCC (23 nucleotides: SEQ ID NO: 17). With such techniques, transposase expression can be evaluated.

[Lane description] 1: molecular weight marker (λHindIII); 2: 97SPi (a); 3: 95SP (a); 4: 97SPi (b); and 5: 95SP (b)

Figure 6:
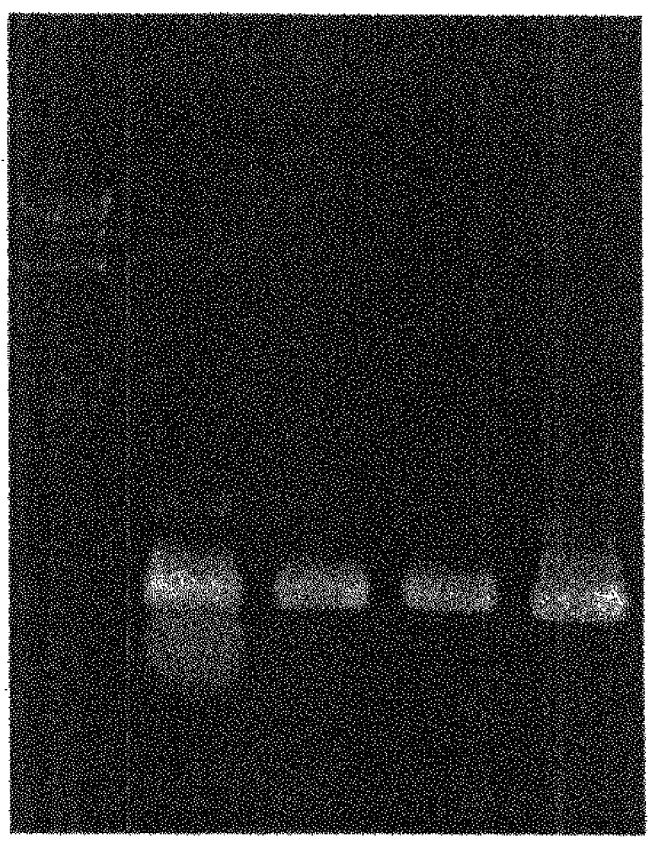

FIG. 6 shows confirmation of the presence or the absence of a transposon in various plants of the genus *Dianthus*. PCR was performed using 2 primers, GGTCTAGTTAGTCAGC-TACGG (21 nucleotides: SEQ ID NO: 16) and CGCAAATA-CACTAAATTTATGCC (23 nucleotides: SEQ ID NO: 17). The presence of the transposon of the present invention was then examined for plants of the genus *Dianthus*. Thus, it was revealed that the transposon is present in another carnation variety (lane 3) and plants (lanes 4 and 5) of the genus *Dianthus* other than carnations.

[Lane description] 1: molecular weight marker (λHindIII); 2: 97SPi; 3: carnation variety Kaly; 4: *Dianthus chinensis*; 5: *Dianthus barbatus*

Figure 7:
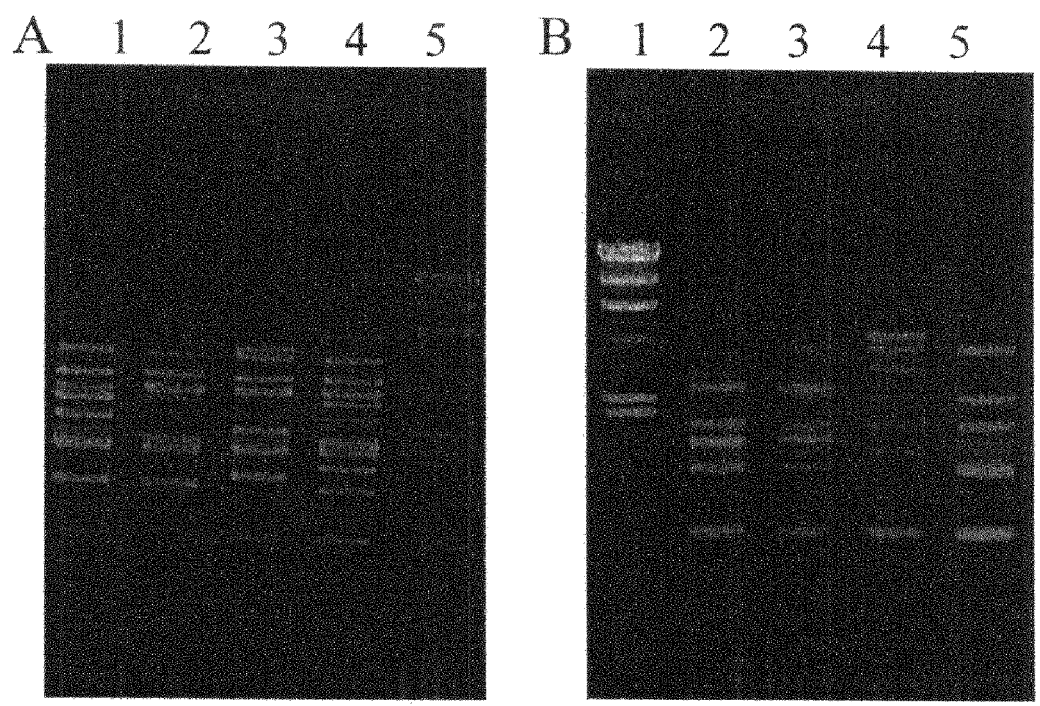

FIG. 7 shows confirmation of the presence or the absence of transposition (bud mutation) of the transposon in various carnation plants. The genomic DNAs of the clone 95SP and 97SPi were digested with a restriction enzyme Hind III or Spe I. The genomic DNAs of clones 99SP4 and 99SP5 that are bud mutants derived from the clones 95SP and 97SPi, respectively, were digested with a restriction enzyme Hind III or Spe I as well (shown in FIGS. 7-A and 7-B, respectively). Inverse PCR was performed using these digested products as materials and primers CGAATACCGTGCTTTGGACG (20 nucleotides: SEQ ID NO: 18) and CGCAAATACAC-TAAATTTATGCC (23 nucleotides: SEQ ID NO: 17). The transposition of the transposon of the present invention was then evaluated. Changes in band pattern varied depending on the clones. Hence, the transposition of the transposon of the present invention was detected.

[Lane description] A Hind III

1: 97SPi; 2: 95SP; 3: 99SP5; 4: 99SP4; and 5: molecular weight marker (λHind III)

[Lane description] B Spe I

1: molecular weight marker (λHind III); 2: 97SPi; 3: 95SP; 4: 99SP5; and 5: 99SP4

BEST MODE OF CARRYING OUT THE INVENTION

Transposon Inducing Bud Mutation

The pink flower color carnation 97SPi is a bud mutant obtained from the purple flower color carnation 95SP. The flower color pigments of the two were analyzed by TLC. Thus, it was revealed that the former flower color pigment has the pelargonidin backbone and the latter has the cyanidin backbone. Accordingly, the causative gene of this bud mutation was considered to be flavonoid 3' hydroxylase. PCR was performed using primers AAGCATATTGCNTAYAAYTAY-CANGA (26 nucleotides: SEQ ID NO: 5) and CCATCTCT-TGCDATNGCCCANAYRTT (26 nucleotides: SEQ ID NO: 6) prepared based on the cDNA sequence (GenBank AX028819) of flavonoid 3' hydroxylase. Thus, the cDNA sequence of 95SP flavonoid 3' hydroxylase was obtained. Here, nucleotides Y, R, and N indicate C or T, A or G, and an arbitrary nucleotide (A, G, C, or T), respectively. The same applies to the following examples. Next, inverse PCR was performed using primers TAAACGGGTACCACATTCCCA (21 nucleotides: SEQ ID NO: 7) and AAGTCGGAAAAC-CTCTTTGAT (21 nucleotides: SEQ ID NO: 8) prepared based on the obtained cDNA sequence. Based on the nucleotide sequences that had been revealed so far, 2 combinations of primers were prepared: primers AGCAGGAACAAAGC-CAGTACA (21 nucleotides: SEQ ID NO: 9) and GTTAA-CAATTCAATACTCAGTACA (24 nucleotides: SEQ ID NO: 10) and primers AATGTCACCCTTAGAGGTAACTTTCTA (27 nucleotides: SEQ ID NO: 11) and TAGCAAGGCCT-TAATTTCTGTG (22 nucleotides: SEQ ID NO: 12). The genomic nucleotide sequence of the flavonoid 3' hydroxylase gene was obtained by the PCR products. Moreover, primers CACACGATTCGTTTGCGACC (20 nucleotides: SEQ ID NO: 13) and TAAACGGGTACCACATTCCCA (21 nucleotides: SEQ ID NO: 7) were designed based on the genomic nucleotide sequence of the flavonoid 3' hydroxylase gene, which had previously been revealed. Inverse PCR was performed using the genomic DNA as a material. 97SPi products and 95SP products were compared, so that a DNA fragment specifically existing in 97SPi was obtained.

Furthermore, PCR was performed using a primer GAGACTCATAGTGGTTATATACA (23 nucleotides: SEQ ID NO: 14) prepared based on the nucleotide sequence of the DNA fragment and a primer TAACAACACGTAAC-CGAAAATATA (24 nucleotides: SEQ ID NO: 15) prepared based on the nucleotide sequence of the flavonoid 3' hydroxylase gene. Thus, DNA (that is absent in 95SP) to be inserted into the genomic gene of 97SPi flavonoid 3' hydroxylase was obtained and then the nucleotide sequence was determined. The nucleotide sequence is provided with characteristics of a transposon. Specifically, inverted repeat sequences each consisting of 13 nucleotides were separately present on one end and on the other end. Furthermore, nucleotide sequences each consisting of 8 nucleotides (AGTTAATT), being identical, and being oriented in the same direction were separately present on one side and on the other side of the position where the insertion sequence was present.

Furthermore, an open reading frame was present in the nucleotide sequence. When a homology search was performed for the sequence, no homology was detected at the nucleotide level. However, when a homology search was performed for the amino acid sequence converted from the nucleotide sequence, the amino acid sequence showed homology with that of transposase encoded by a transposon derived from snapdragon or the same derived from maize. Of these results, a result of a homology comparison with snapdragon Tam3 at the amino acid level are shown in FIG. 2. When analysis by BLAST search was performed, homology between the two was found to be 29%.

DNA isolated from the flower petal developing a purple flower color as a result of partial atavism from 97SPi plant was tested by PCR. The inserted nucleotide sequence had been excised. It was revealed that the nucleotide sequence retained transposition ability even after generation of 97SPi.

The nucleotide sequence is shown in SEQ ID NO: 4 and the amino acid sequence of a corresponding transposase portion is shown in SEQ ID NO: 3. The transposon is classified as an autonomous transposon belonging to hAT family. Thus, a non-autonomous transposon having the nucleotide sequence shown in SEQ ID NO: 1 on the 5' end and having the nucleotide sequence shown in SEQ ID NO: 2 on the 3'end (wherein the sequences shown in SEQ ID NO: 1 and SEQ ID NO: 2, respectively, are directly ligated to each end or ligated to each end via an arbitrary linker that is shorter than 4000 nucleotides) can also induce bud mutation via the supply of transposase from outside. PCR was performed using 97SPi genomic DNA as a template and primers AGATCTA-GAGCTGGCAAACCGGTGC (25 nucleotide: SEQ ID NO: 23) and AGATCTAGAGCTGGCAAAAAAACGGGC (27 nucleotide: SEQ ID NO: 24) prepared based on the nucleotide sequence of SEQ ID NO: 4. The nucleotide sequence of the thus-obtained product was then determined. Therefore, a naturally existing non-autonomous transposon lacking transposase gene shown in SEQ ID NO: 22 was obtained. The non-autonomous transposon was also present in 95SP and 97SE that was a mutant derived from 95SP. Furthermore, in the case of 97SE, insertion was observed in a genome site that is absent in 95SP. Thus, it is clear that this transposon is mobile. Furthermore, the nucleotide sequence at the genome site at which insertion specifically into 97SE had been observed was determined. As a result, the nucleotide sequence was found to have inverted repeat sequences each consisting of 13 nucleotides shown in SEQ ID NO: 1 and SEQ ID NO: 2, respectively, being separately present on one end and on the other end, and being homologous to the transposon having a transposase gene. Furthermore, nucleotide sequences each consisting of 8 nucleotides (GTTATATG), being identical, and being oriented in the same direction were separately present on one side and on the other side of the position at which the non-autonomous trasposon had been inserted.

It is predicted that such naturally existing non-autonomous transposon can also induce bud mutation via the supply of transposase of the transposon of the present invention having a transposase gene.

In addition to the nucleotide sequences of SEQ ID NO: 4 and SEQ ID NO: 22, examples of a nucleotide sequence that is used in the present invention include:

(1) a nucleotide sequence encoding a polypeptide having the amino acid sequence of SEQ ID NO: 3;

(2) a nucleotide sequence encoding a polypeptide that has an amino acid sequence derived from the amino acid sequence of SEQ ID NO: 3 by deletion, substitution, insertion, or addition (to either one or both ends) of 1 or several amino acids, and that has activity of making transposition;

(3) a nucleotide sequence ranging from nucleotide 1056 (A) to nucleotide 3497 (T) in the nucleotide sequence of SEQ ID NO: 4;

(4) a degenerate isomer of the nucleotide sequence shown in SEQ ID NO: 4; and (5) a nucleotide sequence hybridizing under stringent conditions to the nucleotide sequence according to any one of (1) to (3) above, the degenerate isomer according to (4) above, or SEQ ID NO: 4 and encoding a polypeptide having activity of making transposition, and a nucleotide sequence hybridizing under stringent conditions to SEQ ID NO: 22.

Furthermore, the present invention also encompasses any one of the following polypeptides (1) and (2):

(1) a polypeptide having the amino acid sequence of SEQ ID NO: 3; and (2) a polypeptide having an amino acid sequence derived from the amino acid sequence of SEQ ID NO: 3 by deletion, substitution, insertion, or addition (to either one or both ends) of 1 or several amino acids and having transposase activity.

Such deletion, substitution, insertion, or addition (to either one or both ends) of amino acids in (2) above can be easily implemented by persons skilled in the art by a site-specific mutagenesis method or the like as described in D. F. Mark et al, Proc. Natl. Acad. Sci. U.S.A. 81 (1984) 5662-5666; S. Inouye et al, Proc. Natl. Acad. Sci. U.S.A. 79 (1982) 3438-3441; WO85/00817; and R. P. Wharton et al, Nature 316 (1985) 601-605, for example. A polypeptide having the thus-obtained mutant amino acid sequence may be the polypeptide of the present invention, as long as it has activity of making transposition to induce bud mutation. The presence or the absence of the activity of making transposition can be determined by methods described in the following examples.

The degenerate isomer in (4) above means a nucleotide sequence that can encode the same polypeptide although it differs in terms of degenerate codons only. In a nucleotide sequence that is referred as a degenerate isomer in the present invention, for example, a codon AAC (that is, an example of a codon corresponding to any one of the amino acids of the amino acid sequence encoded by a nucleotide sequence) corresponding to Asn has been altered to AAT (that is in degenerate relationship with AAC).

The stringent conditions in (5) above are conditions of a sodium concentration between 10 mM and 300 mM and preferably between 20 mM and 100 mM, and a temperature between 25° C. and 70° C. and preferably 42° C. and 55° C. [Molecular Cloning (edited by Sambrook et al., (1989) Cold Spring Harbor Lab. Press, New York)].

Furthermore an example of a nucleotide sequence that is used in the present invention is also a nucleotide sequence having 80% or more, preferably 90% or more, more preferably 94% or more, and most preferably 99% or more homology with the nucleotide sequence of the above SEQ ID NO: 4 or SEQ ID NO: 22 s long as it has an ability to transpose. Such numerical values representing homology are calculated using a program for nucleotide sequence comparison (e.g., DNA-SIS-Mac v3.7 BLAST: NCBI website (www.ncbi.nlm.nih.gov/entrez/)) and default (initial setting) parameters.

The strength of the activity of DNA containing a nucleotide sequence encoding transposase or of mutants of such portion is not specifically limited, as long as they have activity of making transposition. It is preferable that each of them substantially has activity of making transposition equivalent to that of the DNA containing the nucleotide sequence or the portion thereof. Here, "substantially has the activity" means, in embodiments of the actual use of the activity, that the activity is maintained to some extent such that almost the same use thereof is possible under the same conditions as those employed for the DNA and the portion. Furthermore, "activity" used herein means the activity in plant cells or plants, preferably the same in the cells or the plants of dicotyledons, and more preferably the same in the cells or plants of carnations, for example. Here, transposition activity can be measured according to methods such as Hashida et al's method [as reported in Plant Pysiol. 132: 1207-1216]. This method involves preparing a plasmid containing a transposon that has lacked autonomy because of deletion, introducing the plasmid by bombardment into cells, and then observing frequency of transposition from the plasmid.

Furthermore, primers were prepared based on SEQ ID NO: 4 among the thus-obtained transposons and then PCR was performed. Amplification products of expected sizes were obtained not only in the case of carnation variety Kaly, but also in the cases of *Dianthus chinensis* and *Dianthus barbatus*. It is clear that this transposon is present at least in plants of the genus *Dianthus*. Furthermore, any transposons that have transposase activity and can cause transposition as described above are included herein, in addition to those of the genus *Dianthus* discovered in the present invention. Thus, mutation phenomena such as flower color mutation in a wide range of plants can be explained due to such transposons. Examples of such plants include, but are not limited to, plants of the family Caryophyllaceae that includes the genus *Dianthus*, the family Rosaceae, the family Nyctaginaceae, the family Asteraceae (Compositae), the family Convolvulaceae, the family Balsaminaceae, and the family Solanaceae, in addition to those of the genus *Dianthus*. Moreover, such transposon may be found in a broader range, such as in monocotyledons and dicotyledons.

Primers to be used for detection of the presence or the absence of a transposon can be designed by arbitrarily selecting 2 portions of the nucleotide sequence of a transposon. Specifically, each portion consists of 8 or more continuous nucleotides, desirably 16 or more continuous nucleotides, further desirably 20 or more continuous nucleotides, and further preferably 20 to 30 nucleotides. Primer sequences used in the following examples are GGTCTAGTTAGT-CAGCTACGG (21 nucleotides: SEQ ID NO: 16) and CGCAAATACACTAAATTTATGCC (21 nucleotides: SEQ ID NO: 17). However, sequences other than such sequences may also be used. Distance between positions of two selected primers can be appropriately 100 to 1000 nucleotides, and further preferably 300 to 600 nucleotides. The primers may be those capable of amplifying target DNA fragments between themselves. For example, such primers can be arbitrarily selected using an analytical software such as GENE-TYX-WIN version 4.0 and then used. Such primers can be used for the detection of the present invention using a gene amplification method such as PCR, as long as they enable several kinds of or desirably 1 kind of amplified product to be obtained. An example of such a gene amplification method is, but is not limited to, the PCR method. Any amplification method using specific primers can be used. Persons skilled in the art can easily perform the PCR method by referring to, for example, the Gene Amplification PCR Method, KYORITSU SHUPPAN CO., LTD. (1990).

An adaptor sequence can also be added to a primer, in addition to specific portions (see Examples) designed from SEQ ID NO: 4 and SEQ ID NO: 22. Examples of a PCR method that involves such addition of an adaptor sequence include, but are not limited to, a PCR-AFLP method and a PCR-VECTORETTE method. A PCR-SSR method focusing on the number of repetitions of CT, a PCR-SSCP method focusing on differences in higher order structures depending on nucleotide sequences, a PCR-DGGE method focusing on differences in melting temperatures of double-stranded DNAs, and the like can also be appropriately used. These techniques can be easily selected and performed by persons skilled in the art.

As a probe that is used for detecting the presence or the absence of a transposon, a DNA fragment containing at least 100 continuous nucleotides of the nucleotide sequence of SEQ ID NO: 4 or SEQ ID NO: 22 or of the nucleotides of (1) to (5) above or a probe containing 100 nucleotides having a complementary sequence thereof can be used. A probe can be labeled by generally employed means such as radioactivity labeling (Amersham megaprime method) and DIG labeling (according to the method of F. Hoffmann-La Roche Ltd.).

Furthermore, when a gene wherein a transposon has been inserted can be identified, excision of the transposon can be confirmed as follows. For example, Southern hybridization is performed using a transposon obtained according to the present invention as a probe. Alternatively, inverse PCR is performed using primers prepared based on the nucleotide sequence of such transposon. By detecting differences between the resulting mutant and a plant from which the mutant has been derived, a portion (fragment) of a mutant gene (wherein the transposon has been inserted) can be isolated. The entire mutant gene can be easily isolated using the thus-obtained DNA fragment.

Primers that are used for detecting the excision or the lack of excision of a transposon can be designed by arbitrarily selecting two portions consisting of 8 or more continuous nucleotides, desirably 16 or more continuous nucleotides, further desirably 20 or more continuous nucleotides, and even further desirably 20 to 30 nucleotides from the nucleotide sequence of a transposon and the nucleotide sequence encoding an enzyme for flower color expression (here, this means the genomic nucleotide sequence of a flavonoid 3' hydroxylase gene), when the relevant transposon has been inserted into such nucleotide sequence encoding the enzyme for flower color expression, for example. Primer sequences used in the following examples are GTTAACAATTCAATACT-CAGTACA (24 nucleotides: SEQ ID NO: 10) and GGTCTAGTTAGTCAGCTACGG (21 nucleotides: SEQ ID NO: 16), respectively, derived from the nucleotide sequences shown in SEQ ID NO: 19 and SEQ ID NO: 4, respectively. Primer sequences other than these may also be used. Any primers can be used herein, as long as they allow amplification of a target DNA fragment between such primers. For example, such primers can be arbitrarily selected using analytical software such as GENETYX-WIN version 4.0 and then used.

Such primers that enable several kinds of and desirably 1 kind of amplified product to be obtained can be used for the detection of the present invention using a gene amplification method such as PCR. An example of such a gene amplification method is, but is not limited to, the PCR method. Any amplification method using specific primers can be used. For example, persons skilled in the art can easily perform the PCR method by referring to the Gene Amplification PCR Method, KYORITSU SHUPPAN CO., LTD. (1990).

Furthermore, the present invention also encompasses the following methods:

(1) a method for detecting the presence or the absence of bud mutation, which comprises detecting a transposon having the nucleotide sequence shown in SEQ ID NO: 1 on the 5' end and having the nucleotide sequence shown in SEQ ID NO: 2 on the 3' end, a DNA according to [A] below, or the nucleotide sequence of a transposon according to [B] below by a gene amplification method using a primer containing at least 8 continuous nucleotides of the nucleotide sequence of SEQ ID NO: 4 or SEQ ID NO: 22, wherein

[A]: a DNA, which comprises any one of the following nucleotide sequences (a) to (d), (f), and (g), or the following degenerate isomer (e):

(a) a nucleotide sequence encoding a polypeptide having the amino acid sequence of SEQ ID NO: 3;

(b) a nucleotide sequence encoding a polypeptide that has an amino acid sequence derived from the amino acid sequence of SEQ ID NO: 3 by deletion, substitution, insertion, or addition (to either one or both ends) of 1 or several amino acids, and that has transposase activity;

(c) the nucleotide sequence of SEQ ID NO: 4;

(d) a nucleotide sequence ranging from nucleotide 1056 (A) to nucleotide 3497 (T) in the nucleotide sequence of SEQ ID NO: 4;

(e) a degenerate isomer of the nucleotide sequence of SEQ ID NO: 4;

(f) a nucleotide sequence hybridizing under stringent conditions to the nucleotide sequence according to any one of (a) to (d) above or the degenerate isomer according to (e) above and encoding a polypeptide that has activity of making transposition; and (g) either one of the following nucleotide sequences (i) and (ii)

(i) the nucleotide sequence of SEQ ID NO: 22; and (ii) a nucleotide sequence hybridizing under stringent conditions to the nucleotide sequence according to (i) above;

[B]: a non-autonomous transposon, which has the nucleotide sequence shown in SEQ ID NO: 1 on the 5' end and has the nucleotide sequence shown in SEQ ID NO: 2 on the 3' end, wherein the sequences shown in SEQ ID NO: 1 and SEQ ID NO: 2 are directly ligated to each end or ligated to each end via an arbitrary linker that is shorter than 4000 nucleotides.

(2) a method for detecting the presence or the absence of a transposon having the nucleotide sequence shown in SEQ ID NO: 1 on the 5' end and having the nucleotide sequence shown in SEQ ID NO: 2 on the 3' end, a transposon having the DNA according to [A] above, or a transposon according to [B] above by a gene amplification method using a primer containing at least 8 continuous nucleotides of the nucleotide sequence of SEQ ID NO: 4 or SEQ ID NO: 22.

(3) a method for detecting the excision or the lack of excision of a transposon having the nucleotide sequence shown in SEQ ID NO: 1 on the 5' end and having the nucleotide sequence shown in SEQ ID NO: 2 on the 3' end, a transposon having the DNA according to [A] above, or a transposon according to [B] above by a gene amplification method using a primer containing at least 8 continuous nucleotides of the nucleotide sequence of SEQ ID NO: 4 or SEQ ID NO: 22 and a primer containing at least 8 continuous nucleotides of the nucleotide sequences surrounding the portion where the transposon has been inserted.

More specifically, the present invention also encompasses a method for detecting the excision or the lack of excision of a transposon having the nucleotide sequence shown in SEQ ID NO: 1 on the 5' end and the nucleotide sequence shown in SEQ ID NO: 2 on the 3' end, a transposon having the DNA according to [A] above, or the transposon according to [B] above by the PCR method using an arbitrary portion consisting of at least 8 continuous nucleotides of the nucleotide sequence of SEQ ID NO: 4 and an arbitrary portion consisting of at least 8 continuous nucleotides of the nucleotide sequence of SEQ ID NO: 19 as primers. The present invention also encompasses:

(4) a method for detecting the presence or the absence of bud mutation, which comprises detecting a transposon having the nucleotide sequence shown in SEQ ID NO: 1 on the 5' end and having the nucleotide sequence shown in SEQ ID No: 2 on the 3' end, a transposon having the DNA according to [A] above, or the nucleotide sequence according to [B] above by the use of a probe containing at least 100 continuous nucleotides of the nucleotide sequence of SEQ ID NO: 4 or SEQ ID NO: 22 or containing 100 nucleotides having a complementary sequence thereof; and (5) a method for detecting the presence or the absence of a transposon having the nucleotide sequence shown in SEQ ID NO: 1 on the 5' end and having the nucleotide sequence shown in SEQ ID NO: 2 on the 3' end, a transposon having the DNA according to [A] above, or the transposon according to [B] above by the use of a probe containing at least 100 continuous nucleotides of the nucleotide sequence of SEQ ID NO: 4 or SEQ ID NO: 22 or containing 100 nucleotides having a complementary sequence thereof.

Explanation concerning these detection methods (1) to (5) is as follows.

Detection of Bud Mutation

Mutants can be easily detected by examining differences between mutants and an original individual plant using a technique such as Southern hybridization, inverse PCR, or transposon display using the nucleotide sequences of the transposons of the present invention.

In the following examples, mutation was detected using inverse PCR. A restriction enzyme used herein was Hind III or Spe I. Primers used herein were CGAATACCGT-GCTTTGGACG (20 nucleotides: SEQ ID NO: 18) and CGCAAATACACTAAATTTATGCC (23 nucleotides: SEQ ID NO: 17). However, those other than such enzymes and primers may also be used. A restriction enzyme that can be used in the detection of the present invention has no cleavage site between a site at the 3' end of a primer and a site of the 3' end of another primer, and also has no cleavage site between the 3' end of one primer and the 3' end of a transposon. A primer to be used in the detection of the present invention can be obtained by arbitrarily selecting two portions that are oriented in opposite directions, each consisting of 8 or more continuous nucleotides, desirably 16 or more continuous nucleotides, further desirably 20 or more continuous nucleotides, and further preferably 20 to 30 continuous nucleotides from the nucleotide sequence of the transposon. Such primers may be used herein, as long as they enable amplification of target. DNA fragments between the primers. For example, primers can be arbitrarily selected using analytical software such as Oligo 4.0 and then used.

Mutation Due to Promotion of the Transposition of a Transposon that Induces Bud Mutation (1) Method for Using a Transposon As environmental conditions that induce the transposition of a transposon, callus culture, ultraviolet irradiation, radiation irradiation, pathogenic microbial infection, and the like are known (Plant Cell 1998; 10: 427-34). Furthermore, temperature conditions such as low temperature (MGG 1987; 207: 82-89) and high temperature (JP Patent Publication (Kokai) No. 2003-93074 A) conditions have also been reported as factors that promote transposition. As such, it has been revealed that transposition of a transposon is activated by various environmental or artificial factors. By exposing of plants to such conditions, the transposition of a transposon (mutation induction) can be promoted.

The transposons obtained in the present invention having the nucleotide sequences of SEQ ID NO: 4 and SEQ ID NO: 22 are actually transposable. Furthermore, it has been revealed at the DNA level that bud mutation can be induced by transposition of each of these transposons. The transposition of the transposons obtained according to the present invention and inserted in flavonoid 3' hydroxylase gene of 97SPi is significantly promoted under at least low temperature conditions, short day conditions, or a combination of low-temperature and short-day conditions. However, the conditions are not limited thereto. Thus, it becomes possible to efficiently obtain bud mutants with the above promotion. Furthermore, as described above, conditions such as callus culture, ultraviolet irradiation, radiation irradiation, pathogenic microbial infection (Plant Cell 1998; 10: 427-34), or high temperature (JP Patent Publication (Kokai) No. 2003-93074 A) are also candidates for promoting transposition of the transposons of the present invention.

Furthermore, it is known that a transposon's own demethylation is involved in promotion of the transposition thereof (Plant Growth Regulations 2001; 36: 178-180). It is thought that the transposition of a transposon can be promoted by suppressing the expression of a DNA methylase gene or treating with a chemical substance such as 5-azacytidine so as to promote demethylation. For easy detection of such conditions to activate (transpose) a transposon, it is also effective to examine the transposase activity of plants placed under various conditions.

Hence, bud mutation can be efficiently introduced by exposing plants confirmed as having transposons via screening to the above conditions for inducing transposition or by chemically treating the same.

The transcription level of transposase can be estimated by examining the amount by Northern hybridization or return PCR, by which factors that promote transposition can be easily specified and conditions for obtaining bud mutation can be determined. Moreover, the methylation degree of a transposon can be easily tested by the use of a DNA polymorphism detection method such as RFLP, AFLP, or CAPS using a methylation-sensitive restriction enzyme and a methylation-non-sensitive restriction enzyme (Nature (2001) 411: 212-214). Such methylation degree can also be tested by decoding the nucleotide sequence after chemical conversion of cytosine residues to uracil residues without affecting any methylcytosine residues (Nucleic Acids Res (1994) 22: 2990-2997). Such evaluation can be easily performed by persons skilled in the art.

Through monitoring of the transposase transcription levels and through evaluation of the methylation degree of such transposons, evaluation of the transposition activity of transposons is made possible. Thus, conditions for promoting transposition can be easily obtained.

The present in invention also encompasses a method for producing a bud mutant, that is, a method for inducing bud mutation, which comprise genetically transforming a host using the DNA according to the invention to produce a transformant (DNA which expresses the gene) causing transposase expression, and then promoting the transposition of a transposon regardless of whether it is an autonomous or non-autonomous transposon. Such methods will be explained in the following (2) to (4).

(2) DNA Containing a Gene Encoding Transposase

Not only a transposase-encoding gene's own promoter but also a promoter other than a transposase-encoding gene's own promoter can be used. Such gene's own promoter is exchanged with a promoter confirmed to be able to function in plants, such as cauliflower mosaic virus 35S promoter. Then the resultant transposase-encoding gene is introduced into a plant by a gene transfer technique. Bud mutation can thus be promoted by causing the transposition of any one of the nucleotide sequences of the invention.

Here, a cauliflower mosaic virus 35S promoter is exemplified as a promoter. However, examples of promoters are not limited to such a promoter, as long as they are capable of functioning in plants.

Furthermore, transposition can be promoted only under inducing conditions by linking a gene to an inducible promoter and then introducing the resultant gene into a plant using a gene transfer technique. Transposition can also be promoted by causing transient expression of a gene encoding transposase without genetic recombination.

As an inducible promoter, a promoter having heat-shock inducibility (Appl Microbiol Biotechnol. 1995 44: 466-472) can be used, for example. However, examples of promoters are not limited to the above promoters. Any promoter may be used herein, as long as it is inducible and capable of functioning within plant cells or plants.

Moreover, the above promoter can be obtained by PCR amplification reaction using primers designed based on the nucleotide sequence of DNA containing the promoter and genomic DNA as a template. Specifically, an inducible promoter can be obtained by amplification of the promoter region (region at -678 from the translation initiation point of a heat shock protein gene) of a heat shock protein gene (Mol Gen Genet (1989) 219: 365-372) that is one of the above-mentioned genes by polymerase chain reaction (PCR). An example of a template DNA that can be used for PCR is, but is not limited to, the genomic DNA of *Arabidopsis thaliana*.

As such promoters, various mutant promoters can be used as in the case of the above genes of transposons, as long as they have promoter activity. By referring to the nucleotide sequences described in documents concerning the various promoters mentioned above, such mutated promoters can be obtained by persons skilled in the art without any special difficulty, as in the description concerning the above genes of transposons. Whether or not a mutated promoter obtained as described above has promoter activity and whether or not DNA containing a promoter or a portion thereof actually retains promoter activity can be confirmed by ligating a transposon gene thereto, causing the expression of the resultant within host cells, and then performing the above bud mutation detection method, visual inspection, or analysis of biological components, such as flower pigment analysis. Such methods can be easily performed by persons skilled in the art.

Furthermore, a terminator that directs transcriptional termination can also be ligated downstream of a gene encoding transposase, if necessary.

Examples of terminators include 35S gene, nos gene, and ocs gene terminators (Annu. Rev. Plant Physiol. Plant Mol. Biol., 44 (1993) 985-994, "Plant genetic transformation and gene expression; a laboratory manual"). Examples of terminators are not specifically limited to the above terminators, as long as they are terminators that are known to be capable of functioning within plant cells or plants.

Furthermore, an intron sequence having a function of enhancing gene expression, such as an alcohol dehydrogenase (Adh1) intron of maize[Genes & Development 1: 1183-1200 (1987)] can be introduced between a promoter sequence and a gene of transposon, if necessary.

DNA can further contain components such as a translation enhancer and a translation termination codon. As a translation enhancer and a translation termination codon, a known translation enhancer and a known translation termination codon can be appropriately combined and then used. Examples of translation enhancers of viral origin include sequences of tobacco mosaic virus, alfalfa mosaic virus RNA4, bromo mosaic virus RNA3, potato virus X, and Tobacco etch virus (Gallie et al., Nuc. Acids. Res., 15 (1987) 8693-8711). Moreover, examples of translation enhancers of plant origin include sequences derived from soybean β-1,3 glucanase (Glu) (written by Isao Ishida and Norihiko Misawa, edited by Kodansha Scientific Ltd., Introduction to Cell Engineering Experimental Protocols (*Saibo Kogaku Jikken Sosa Nyumon*), Kodansha Ltd., p. 119, 1992), and tobacco ferredoxin-binding subunit (PsaDb) (Yamamoto et al., J. Biol. Chem., 270 (1995) 12466-12470). Examples of translation termination codons include sequences such as TAA, TAG, and TGA [described in the above-mentioned Molecular Cloning and the like]. Furthermore, it has been reported that activity can be enhanced by ligation of a plurality of a portion in the promoter identified as a 35S gene enhancer portion, that is, transcriptional enhancer (Plant Cell, 1 (1989) 141-150). Such portion can also be used as a part of DNA. Such various components are preferably incorporated into a DNA strand so that each of them can function (or can exert its property). Such operation can be appropriately performed by persons skilled in the art.

The above DNA can be easily produced by persons skilled in the art using techniques commonly employed in the field of genetic engineering. Furthermore, the DNA of the present invention is not limited to those isolated from natural sources. Such DNA may be an artificial construct, as long as it has the above-mentioned structure. Such DNA can be obtained by synthesis according to a known and commonly employed method for nucleic acid synthesis.

(3) Transformation and Confirmation of Gene-Expressing Plant

A protein having enzymatic activity as a transposon can be expressed by transforming a host with the above transposon gene and then culturing or cultivating the thus-obtained transformant. Furthermore, by transposition and insertion of the transposon, a mutant can be produced wherein the expression of the activity of a gene encoding an arbitrary enzyme has been suppressed.

A post-transformation strand of the present invention can be present in microorganisms (particularly, bacteria), phage particles, or plants after insertion into a plasmid, a phage, or a genomic DNA. Here, typical examples of bacteria include, but are not limited to, *Escherichia coli* and *Agrobacterium*.

In a preferable embodiment of the present invention, to enable stable expression of a structural gene for protein expression within plant cells or plants, the DNA of the present invention, a translation enhancer, a translation termination codon, a terminator, and the like are linked, so that the linked product is present in a plant after insertion into the genome.

Preferable examples of hosts include plant cells of monocotyledons such as rice, wheat, maize, *Allium*, lily, and orchid, and plant cells of dicotyledons such as soybean, rapeseed, tomato, potato, chrysanthemum, rose, carnation, petunia, *Gypsophila*, and *Cyclamen*. Particularly preferable specific examples of hosts include plant cells of chrysanthemum, carnation, and rose that are three major cut flowers characterized by production, distribution, and consumption in significant quantities throughout the world. As clones, such specific examples also include plant cells of petunia and the like characterized by recently drastically increasing quantities of production, distribution, and consumption throughout the world, among clonally propagated plants. Furthermore, specific examples of plant materials include growing points, shoot primordium, meristems, leaf sections, stem sections, root sections, tuber sections, petiole sections, protoplasts, calli, anthers, pollens, pollen tubes, peduncle sections, scape sections, petals, and sepal sections.

As a method for introducing a foreign gene into a host, various previously reported and established methods can be appropriately used. Preferable examples of biological methods therefor include methods that use a Ti plasmid, an Ri plasmid of *Agrobacterium*, or the like of a virus as a vector. Preferable examples of physical methods therefor include methods that involve introducing a gene by electroporation, polyethylene glycol, particle gun, microinjection (the above-mentioned "Plant Genetic Transformation and Gene Expression; A Laboratory Manual"), silicon nitride whisker, or silicon carbide whisker (Euphytica 85 (1995) 75-80, In Vitro Cell. Dev. Biol. 31 (1995) 101-104, Plant Science 132 (1998) 31-43). Such introduction method can be appropriately selected and used by persons skilled in the art.

Furthermore, by causing regeneration from plant cells that have been transformed with the DNA of the present invention, a transformant plant expressing the introduced gene within such cells can be produced. Such operation can be easily performed by persons skilled in the art by a method generally known as a method for regeneration of a plant from transformed plant cells. Regeneration of a plant from plant cells can be easily performed by persons skilled in the art by referring to a document entitled, "Plant Cell Culture Manual," edited and written by Yasuyuki Yamada, Kodansha Scientific Ltd., 1984, for example.

In general, a gene introduced into a plant is incorporated into the genome of a host plant. In this case, a phenomenon called position effect is observed, wherein different positions on the genome into which a gene is introduced result in different expression levels of the transgene. A transformant more strongly expressing a transgene can be selected by testing the level of mRNA being expressed in a host plant by the Northern method using a DNA fragment of the transgene as a probe.

Incorporation of a target gene in a transformant plant (wherein a gene to be used in the present invention has been introduced) can be confirmed by extracting DNA from the cells and tissues thereof according to a standard method and then detecting the introduced gene using a known PCR method or Southern hybridization. Moreover, expression in a transformant plant can be easily confirmed by return PCR, for example.

(4) Transient Expression

Transposase gene encoded by the transposon of the present invention is linked to a promoter functioning in plants and then the resultant is transiently expressed. Thus, transposition of the transposon can be promoted only within a limited time, so that mutation can be induced. A system using viruses such as PVX (Plant Cell (1995) 7: 249-257) and a system using *Agrobacterium* (Plant J (2003) 33: 949-956) are known as such transient expression systems, but systems are not limited thereto.

Furthermore, the present invention also encompasses induction of bud mutants via introduction of the nucleotide sequence of SEQ ID NO: 4 or SEQ ID NO: 22 a nucleotide sequence hybridizing under stringent conditions to SEQ ID NO: 4 or SEQ ID NO: 22, and a non-autonomous transposon, which has the nucleotide sequence shown in SEQ ID NO: 1 on the 5' end and has the nucleotide sequence shown in SEQ ID NO: 2 on the 3' end, wherein the sequences shown in SEQ ID NO: 1 and SEQ ID NO: 2 are directly ligated to each end or ligated to each end via an arbitrary linker that is shorter than 4000 nucleotides, into hosts and then supplying transposase so as to promote transposition.

Introduction of DNA into hosts can be easily performed by persons skilled in the art in a manner similar to that of the above-described transformation. Transposition of the thus-introduced DNA can be made possible by crossing with plants (containing the above described transformant) having the DNA a cording to invention or by performing a technique such as the above-described transformation, so as to supply transposase. Bud mutation can a so be induced as described above.

The present invention also encompasses a method for stabilizing bud mutants that are obtained by transposition of a transposon in addition to using the above transformant. This method will be explained as follows.

Stabilization of Bud Mutation

In the case of plants having a transposon within a gene, a revertant cell may be obtained as a result of excision of the transposon from the gene at a frequency greater than that of the incidence of natural mutation. This is called mutability (BIO HORTI, 7, 75-79, 1992, edited by Agriculture and Gardening, SEIBUNDO SHINKOSHA). Mutability is a factor that lowers the stability of agricultural product quality. It is known that when a transposon is excised, several DNA nucleotides of the transposon remain at random in the gene (where the transposon has been present). By the use of this phenomenon, cells wherein the gene function has been disrupted after excision of a transposon can be obtained. Specifically, transposition of a transposon is promoted and then mutants wherein the transposon has been excised from the gene are selected, so that stable mutants can be obtained. Here, as described in "Transposon inducing bud mutation", individual plants wherein a transposon has been excised from a mutated gene can be screened for by PCR using a portion of the transposon and a portion of the mutated gene as primers or by a method described with reference to the above-described detection of bud mutation. Furthermore, such plants can also be screened for through Southern hybridization using the transposon, the mutated gene, or both the transposon and the mutated gene as probes. Regarding the presence or the absence of the several remaining nucleotides derived from the transposon after excision of the transposon, stabilization of bud mutation can be confirmed by amplifying a portion containing the relevant region by a gene amplification method and then directly determining the nucleotide sequence, for example.

In contrast to the above, induction of bud mutation can also be stabilized by avoiding exposure to environmental conditions (e.g., temperature) that promote transposition, or by artificially suppressing transposase expression using a technique such as RNAi.

The present invention also encompasses a method for isolating bud mutants using the above transformants. This method will be explained as follows.

Isolation of Mutated Gene Resulting from Bud Mutation Induced by Transposon

A portion of a mutated gene can be isolated through Southern hybridization using a transposon obtained according to the present invention as a probe or through inverse PCR using primers prepared based on the nucleotide sequence of the transposon and then detecting differences between a mutant and the original plant thereof. The entire mutant gene can be easily isolated using the thus-obtained DNA fragment. The transposon of the present invention is characterized by causing bud mutation. Thus, the transposon can be a tool for gene isolation not only in progeny but also in the generation.

Selection of Mutant Induced by Transposon, Wherein Gene Expression has been Suppressed Suppression of the function of a gene is achieved by genetic engineering using antisense technology or the like. Without using genetic engineering, the transposition of the transposon of the present invention enables the generation of a mutant wherein gene expression has been suppressed. Specifically, transposition of a transposon of a plant having such transposon is caused under low temperature conditions, short day conditions, or a combination of low-temperature and short-day conditions, thereby inducing mutation. Thus, mutants wherein the expression of a gene has been suppressed can be produced. Furthermore, mutants wherein the transposon has been inserted in a target gene can easily be detected (selected) by the PCR method.

Plants wherein a transposon has been inserted into a target gene can easily be selected from a mutant population (that has been induced by the transposon) through Southern hybridization or PCR using the information on a target gene and the DNA of the transposon.

Among the transposons of the present invention, those having transposase therewithin can undergo transposition by themselves (autonomy). It is generally known that even when an internal sequence of a transposon is removed, the transposon can undergo transposition via the supply of transposase [Plant Physiology 132: 1207-1216 (2003)]. For example, according to this document, a transposon can undergo transposition via the supply of transposase, even when 2260 nucleotides from a BalI site to a TthHB81 site are deleted. Accordingly, a transposon lacking transposase activity can be obtained by deleting an internal portion of a transposon. The thus-obtained transposon lacks transposase, so that it cannot undergo transposition by itself. However, it can undergo transposition via the supply of transposase. A transposon internally lacking transposase, which was obtained according to the present invention, is a transposon capable of undergoing transposition via the supply of transposase existing in the nature. It is known that such transposons capable of undergoing transposition via the supply of transposase are present in the natural world. Such transposons are called non-autonomous transposons [PROTEIN, NUCLEIC ACID AND ENZYME 37: 1047-1059 (1992)]. Whether a transposon is autonomous or non-autonomous can be inferred based on the possession or the lack of a transposase gene that can be expressed.

By the removal (deletion) of the whole or a portion of the nucleotide sequence encoding transposase from, or the introduction of mutation such as nucleotide substitution, insertion, or addition (to either one or both ends) into, the transposon of the present invention, transposons wherein transposase cannot function as described above can be easily produced by persons skilled in the art. Moreover, through the Southern hybridization method using the whole or a portion of the DNA sequence of the transposon of the present invention as a probe or PCR method, DNA fragments having homology with the transposon of the present invention can easily be obtained by persons skilled in the art. Through analysis of the nucleotide sequence of the thus-obtained DNA fragment, transposons having mutations in their transposase portions (so that the transposase is unable to function as described above) can be easily produced or found by persons skilled in the art.

Via artificial production or selection from the natural world, transposons having homology with the transposon of the present invention but being unable to undergo transposition by themselves can easily be obtained by persons skilled in the art. Such transposons can undergo transposition via the use of transposase of the present invention. Hence, such transposons lacking transposase activity can be used for the above-described methods, the detection of the bud mutation, mutation induced by the promotion of the transposition of a transposon that induces bud mutation, bud mutation stabilization, identification of mutated genes resulting from bud mutation induced by a transposon, and selection of mutants induced by a transposon, wherein gene expression has been suppressed.

Hereinafter, examples of the present invention will be described in detail. However, the present invention is not limited by these examples. Furthermore, carnation clones 95SP, 97SPi, 97SE, 99SP5, and 99SP4 used in the following examples are conserved at the Plant Laboratory, Kirin Beer Kabushiki Kaisha. These carnation clones are available upon request for distribution as experimental materials. The contact address is: Postal code: 329-1414; Address: 3377, Aza Sarutsuka, Oaza Sotome, Kitsuregawa-machi, Shioya-gun, Tochigi-ken, Japan (Telephone: Country code 81-28-686-0501; Facsimile: Country code 81-28-686-0502).

EXAMPLE 1

Analysis of Carnation Petal Pigments

Carnation petal pigments were analyzed according to the method of Masaatsu Yamaguchi (MINAMI KYUSHU UNIVERSITY Bulletin of the Faculty of Horticulture (1988), Vol. 19, pp. 1-78: Basic Studies on the flower color breeding of Carnations (*Dianthus caryophyllus* L.)). Petals from carnation clones 95SP and 97SPi were each subjected to extraction with 5% acetic acid and 50% ethanol, followed by development with TLC (acetic acid:hydrochloric acid:water=15:3:82). These development images were compared with an image of an extract from carnation petals (variety: Barbara (Hilverda Plant Technology)) having a known pelargonidin 3 glucoside 5 glucoside (Pg3G5G) pigment and compared with an image of an extract from carnation petals (variety: Lilac (SIRI BROTHERS NURSERY, INC.)) having a cyanidin 3 glucoside 5 glucoside(Cy3G5G) pigment. Thus, it could be inferred that 95SP mainly contained a pigment having the cyanidin backbone and 97SPi contained a pigment having the pelargonidin backbone.

EXAMPLE 2

Preparation of Carnation Genomic DNA

The DNAs of carnation clones 95SP, 97SPi, 97SE, 99SP5, and 99SP4 were prepared using in vitro leaf sections as materials by Nucleon PhytoPure (Amersham) according to attached protocols.

In addition, 99SP5 and 99SP4 were obtained by the following techniques and then used as materials. 1000 in vitro plants with a height of approximately 5 cm were subjected to X-ray irradiation with a dose of 4 KR according to a standard method. The plants were acclimatized in a greenhouse. Axillary buds were collected and grown. Axillary buds were collected again from plants that had developed roots and then the buds were grown. Such steps were repeated several times. As a result, two plants (99SP5 and 99SP4) developing pink flowers (plants developing the same flower color as developed by 97SPi) were obtained.

EXAMPLE 3

Preparation of Carnation cDNA

Carnation clone 95SP RNA was prepared according to the method described in Cell Engineering, Separate Volume, Plant Cell Engineering Series 2, Plant PCR Experimental Protocols (1995) 42-43. Then, the cDNA was prepared using RNA isolated from petals by a cDNA synthesis kit (TAKARA BIO INC.) with a 18-nucleotide-long dT primer attached to the kit according to the attached protocols.

EXAMPLE 4

Cloning of Flavonoid 3'hydroxylase (F3'H) Gene and Determination of the Nucleotide Sequence Thereof (1) Cloning of F3'H Gene of Carnation Clone 95SP and Determination of the cDNA Nucleotide Sequence Based on the cDNA sequence of an F3'H gene described in GenBank AX028819, primers AAGCATATTGCNTAYAAYTAYCANGA (26 nucleotides: SEQ ID NO: 5) and CCATCTCTTGCDATNGCCCANAYRTT (26 nucleotides: SEQ ID NO: 6) were prepared. PCR (conditions: 95° C. for 5 minutes; 30 cycles of 95° C. for 30 seconds, 35° C. for 30 seconds, and 72° C. for 1 minute; and 72° C. for 10 minutes) was performed for the total cDNA fraction obtained from in vitro carnation clone 95SP petals using these primers. The thus-obtained amplification product was subjected to TA cloning (PCR Experiment Note (PCR Jikken Note), edited and written by Taketoshi Taniguchi, YODOSHA CO., LTD. (1997)) using a pGEM T vector (produced by Promega Corporation). Hence, a nucleotide sequence of 848 nucleotides was determined using ABI310 (produced by Applied Biosystems). The thus-obtained nucleotide sequence was compared with the above F3'H gene cDNA sequence described in GenBank AX028819. Nucleotide substitution was observed at 5 positions and insertion of 3 nucleotides was observed at 1 position (FIG. 3).

(2) Cloning of F3'H Gene of Carnation Clone 97SPi and Determination of the Genomic DNA Nucleotide Sequence Next, according to Cell Engineering, Separate Volume, Plant Cell Engineering Series 2, Plant PCR Experimental Protocols (1995) 69-72, the genomic DNA of carnation clone 97SPi was digested with a restriction enzyme Nde I. Inverse PCR (conditions: 95° C. for 2 minutes; 30 cycles of 95° C. for 30 seconds, 56° C. for 30 seconds, and 72° C. for 2 minutes; and 72° C. for 3 minutes) was performed using the digested product as a material and primers TAAACGGGTACCACAT-TCCCA (21 nucleotides: SEQ ID NO: 7) and AAGTCG-GAAAACCTCTTTGAT (21 nucleotides: SEQ ID NO: 8) prepared based on the above nucleotide sequence of the F3'H gene obtained from carnation clone 95SP. The thus-obtained amplification product of approximately 1.6 kb was subjected to TA cloning (PCR Experiment Note (PCR Jikken Note), edited and written by Taketoshi Taniguchi, YODOSHA CO., LTD. (1997)) using a pGEM T vector (produced by Promega Corporation). The nucleotide sequence was determined using ABI310 (produced by Applied Biosystems). The nucleotide sequence obtained herein was divided by two at the cleavage site of the restriction enzyme Nde I, thereby resulting in 2 kinds of nucleotide sequence.

Next, the following primers were prepared based on the cDNA sequence described in GenBank AX028819, the cDNA sequence of the carnation clone 95SP F3'H gene revealed in Example 4 (1), and the genomic DNA nucleotide sequence constituting a portion of the carnation clone 97SPi F3'H gene revealed in the previous paragraph. PCR (conditions: 95° C. for 5 minutes; 30 cycles of 95° C. for 30 seconds, 56° C. for 30 seconds, and 72° C. for 3 minutes; and 72° C. for 3 minutes) was performed for the genomic DNA of the carnation clone 97SPi using primers AGCAGGAACAAAGC-CAGTACA (21 nucleotides: SEQ ID NO: 9) and GTTAA-CAATTCAATACTCAGTACA (24 nucleotides: SEQ ID NO: 10). The amplification product of approximately 1.9 kb and an amplification product of approximately 2.9 kb that had been similarly obtained by the use of primers AATGTCAC-CCTTAGAGGTAACTTTCTA (27 nucleotides: SEQ ID NO: 11) and TAGCAAGGCCTTAATTTCTGTG (22 nucleotides: SEQ ID NO: 12) were subjected to TA cloning (PCR Experiment Note (PCR Jikken Note), edited and written by Taketoshi Taniguchi, YODOSHA CO., LTD. (1997)) using a pGEM T vector (produced by Promega Corporation). The nucleotide sequences were determined using ABI310 (produced by Applied Biosystems).

(3) The Genomic DNA Nucleotide Sequence of Carnation F3'H Gene

A total of 5 types of nucleotide sequence (the cDNA sequence in Example 4 (1), 2 kinds of DNA sequence obtained by inverse PCR from the DNA fragment of approximately 1.6 kb in Example 4 (2), the DNA sequence of the DNA fragment of approximately 1.9 kb obtained by PCR in Example 4 (2), and the DNA sequence of the DNA fragment of approximately 2.9 kb obtained by PCR in Example 4 (2)) were linked. Overlap portions were then eliminated. Thus, the genomic DNA nucleotide sequence of 5,743 nucleotides of the carnation F3'H gene was determined (SEQ ID NO: 19). Furthermore, the presence of two F3'H genes was predicted as allelic genes in 97SPi. It was revealed that frame shift took place in 97SPi, wherein G had been inserted following nucleotide A that was nucleotide 2527 of SEQ ID NO: 19.

EXAMPLE 5

Cloning of a Transposon from DNA of Carnation Clone 97SPi and Determination of the Nucleotide Sequence Thereof Inverse PCR was performed according to Cell Engineering, Separate Volume, Plant Cell Engineering Series 2, Plant PCR Experimental Protocols (1995) 69-72. The genomic DNAs were prepared from the carnation clones 95SP and 97SPi by the method described in Example 2 and then digested with a restriction enzyme Hind III. Inverse PCR (conditions: 95° C. for 2 minutes; 30 cycles of 95° C. for 30 seconds, 56° C. for 30 seconds, and 72° C. for 2 minutes; and 72° C. for 3 minutes) was performed using the digested products as materials and primers CACACGATTCGTTTGC-GACC (20 nucleotides: SEQ ID NO: 13) and TAAACGGG-TACCACATTCCCA (21 nucleotides: SEQ ID NO: 7) prepared based on the DNA sequence of 848 nucleotides obtained in Example 4 (1). The thus-obtained amplification products were separated by electrophoresis using 1% agarose gel with 100 V for 20 minutes and then visualized by ethidium bromide staining. As a result, an amplification product of approximately 2.5 kb specifically existing in 97SPi was obtained. The thus-obtained product was subjected to TA cloning (PCR Experiment Note (PCR Jikken Note), edited and written by Taketoshi Taniguchi, YODOSHA CO., LTD. (1997)) using a pGEM T vector (produced by Promega Corporation). The nucleotide sequence was then determined using ABI310 (produced by Applied Biosystems). The nucleotide sequence was divided at the internally existing cleavage site of a restriction enzyme Hind III, thereby resulting in 2 kinds of nucleotide sequence. One of such kinds of nucleotide sequence that was approximately 300 nucleotides in length was identical to a portion of the DNA nucleotide sequence (SEQ ID NO: 19) obtained in Example 4.

Next, PCR (conditions: 95° C. for 2 minutes; 30 cycles of 95° C. for 30 seconds, 56° C. for 30 seconds, and 72° C. for 3 minutes; and 72° C. for 3 minutes) was performed using a primer GAGACTCATAGTGGTTATATACA (23 nucleotides: SEQ ID NO: 14) prepared based on the DNA sequence of approximately 2.5 kb revealed in the previous paragraph, a primer TAACAACACGTAACCGAAAATATA (24 nucleotides: SEQ ID NO: 15) prepared based on the DNA sequence of approximately 1.9 kb obtained in Example 4 (2), and carnation clone 97SPi genomic DNA as a template. The thus-obtained amplification product of approximately 3 kb was subjected to TA cloning (PCR Experiment Note (PCR Jikken Note), edited and written by Taketoshi Taniguchi, YODOSHA CO., LTD. (1997)) using a pGEM T vector (produced by Promega Corporation). The nucleotide sequence was determined using ABI310 (produced by Applied Biosystems).

Two kinds of nucleotide sequence were linked, excluding 1 kind of nucleotide sequence that matched the nucleotide sequence obtained in Example 4 among 3 kinds of DNA nucleotide sequence obtained in this Example.

Overlap portions were eliminated. Then, a portion of 40 nucleotides and a portion of 931 nucleotides that were homologous to the genomic DNA nucleotide sequence (SEQ ID NO: 19) of the flavonoid 3' hydroxylase (F3'H) gene that existed on both ends and that was obtained in Example 4 were eliminated. Therefore, the DNA nucleotide sequence (SEQ ID NO: 4) of the transposon of the present invention was obtained. An open reading frame (ORF) consisted of 2442 nucleotides ranging from nucleotide A (nucleotide 1056) to T (nucleotide 3497) as analyzed by DNASIS-Mac v3.7.

Figure 4:
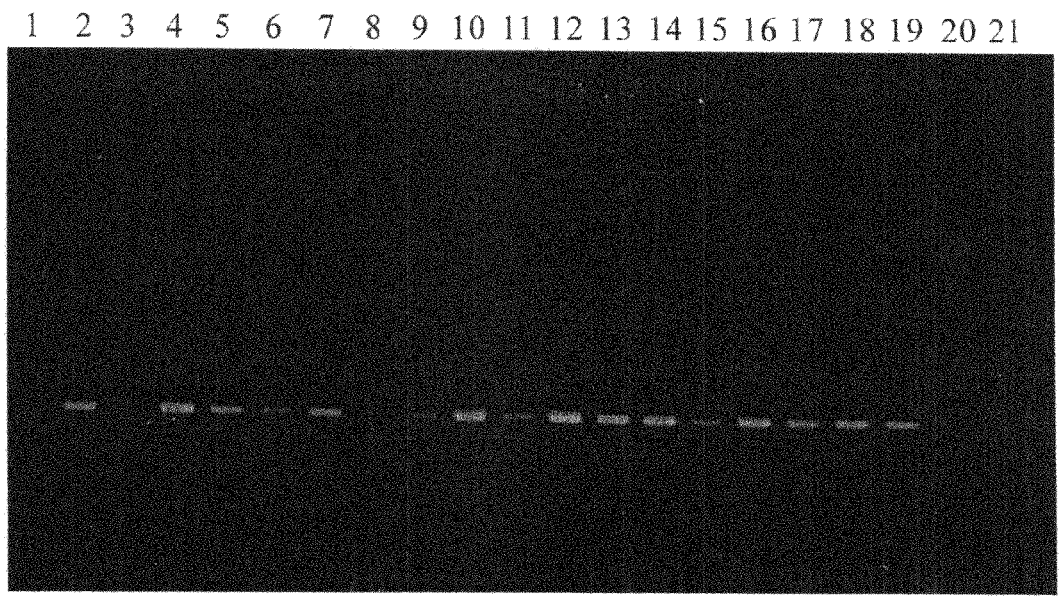
FIG. 4 shows confirmation of the excision or the lack of excision of a transposon in various carnation plants. PCR was performed using 2 primers, GTTAACAATTCAATACT-CAGTACA (24 nucleotides: SEQ ID NO: 10) and GGTCTAGTTAGTCAGCTACGG (21 nucleotides: SEQ ID NO: 16), the DNA of clone 95SP, the DNA of clone 97SPi, or the DNA of the flower petals partially developing a purple flower color as a result of atavism from 97SPi as a template. In the flavonoid 3' hydroxylase gene of 95SP (lane 3), the transposon of the present invention was absent at the position where the same is present in the case of 97SPi. Furthermore, in the flower petals (lanes 20 and 21) developing a purple flower color as a result of atavism, the transposon of the present invention had been excised from the flavonoid 3' hydroxylase gene. It is clear that the transposon of the present invention has transposition ability.

Next, a region between the internal portion of the transposon of the present invention and the portion corresponding to flavonoid 3' hydroxylase was made possible to be amplified by PCR using 2 primers: GTTAACAATTCAATACTCAG-TACA (24 nucleotides: SEQ ID NO: 10) and GGTCTAGT-TAGTCAGCTACGG (21 nucleotides: SEQ ID NO: 16) derived from the DNA nucleotide sequences shown in SEQ ID NO: 19 and SEQ ID NO: 4. PCR (conditions: 95° C. for 2 minutes; 30 cycles of 95° C. for 30 seconds, 56° C. for 30 seconds, and 72° C. for 3 minutes; and 72° C. for 3 minutes) was performed using 95SP and 97SPi DNAs and the DNAs of the flower petals of 97SPi plants that had partially developed a purple flower color as a result of atavism as templates and the above two primers. In the case of 95SP (lane 3) and the flower petals (lanes 20 and 21) that had developed a purple flower color as a result of atavisum, no amplification products were obtained. Thus, it was revealed that the transposon of the present invention had been excised from the flavonoid 3' hydroxylase gene (FIG. 4). Accordingly, it was made clear that the transposon of the present invention has transposition ability.

Furthermore, the nucleotide sequence (wherein nucleotide G had been inserted following nucleotide A (nucleotide 2527) of SEQ ID NO: 19 (flavonoid 3' hydroxylase gene)) that was revealed in Example 4 to relate to the flower color expression of 97SPi was compared with the nucleotide sequences located on either side of the linking nucleotide sequence (SEQ ID NO: 4) of the transposon of the present invention. Thus, it was revealed that the transposon of the present invention had been inserted at following nucleotide T (nucleotide 3908) of SEQ ID NO: 19. It was also revealed that on both sides of the transposon, there were duplicate sequence each consisting of 8 nucleotides of AGTTAATT ranging from nucleotide 3901 to nucleotide 3908 in the nucleotide sequence of SEQ ID NO: 19.

Subsequently, PCR (conditions: 95° C. for 2 minutes; 30 cycles of 95° C. for 30 seconds, 56° C. for 30 seconds, and 72° C. for 2 minutes; and 72° C. for 3 minutes) was performed using 2 primers: AGATCTAGAGCTGGCAAACCGGTGC (25 nucleotides: SEQ ID NO: 23) and AGATCTAGAGCTG-GCAAAAAAACGGGC (27 nucleotides: SEQ ID NO: 24) derived from the revealed nucleotide sequence of the transposon shown in SEQ ID NO: 4 and 97SPi genomic DNA as a template, thereby obtaining amplification products. The products were subjected to TA cloning (PCR Experiment Note (PCR Jikken Note), edited and written by Taketoshi Taniguchi, YODOSHA CO., LTD. (1997)) using a pGEM T vector (produced by Promega Corporation). The nucleotide sequences were determined using ABI310 (produced by Applied Biosystems). Among the obtained amplification products, the amplification product of approximately 0.7 kb is shown in SEQ ID NO: 22. Portions of approximately 0.2 kb each from both ends of the nucleotide sequence were almost homologous to the transposon shown in SEQ ID NO: 4. However, the nucleotide sequence lacked an open reading frame and transposase gene therein. Thus, the nucleotide sequence was determined to be a non-autonomous transposon.

Differences between 95SP and 97SE were examined by inverse PCR. Specifically, the genomic DNA of 95SP and 97SE that was the bud mutant derived from the carnation clone 95SP was prepared according to the method described in Example 2. The DNAs were digested with a restriction enzyme EcoR I. Inverse PCR (conditions: 95° C. for 2 minutes; 30 cycles of 95° C. for 30 seconds, 56° C. for 30 seconds, and 72° C. for 3 minutes; and 72° C. for 3 minutes) was performed using the digested products as materials and primers CGAATACCGTGCTTTGGACG (20 nucleotide: SEQ ID NO: 18) and TCGTGCCGTGCACCGGTTT (19 nucleotides: SEQ ID NO: 25). Inverse PCR was performed according to Cell Engineering, Separate Volume, Plant Cell Engineering Series 2, Plant PCR Experimental Protocols (1995) 69-72. The thus-obtained amplification products were separated by electrophoresis using 1% agarose gel with 100 V for 60 minutes, and then visualized by ethidium bromide staining. As a result, an amplification product of approximately 4.5 kb that was absent in 95SP but was present in 97SE was obtained. The amplification product was subjected to TA cloning (PCR Experiment Note (PCR Jikken Note), edited and written by Taketoshi Taniguchi, YODOSHA CO., LTD. (1997)) using a pGEM T vector (produced by Promega Corporation). The nucleotide sequence was partially determined using ABI310 (produced by Applied Biosystems). PCR (conditions: 95° C. for 2 minutes; 30 cycles of 95° C. for 30 seconds, 56° C. for 30 seconds, and 72° C. for 2 minutes; and 72° C. for 3 minutes) was performed using primers TATACG-GAGTACCACAATCAGA (22 nucleotides: SEQ ID NO: 26) and CTAGTATGCTAGTCTGAAGGC (21 nucleotides: SEQ ID NO: 27) prepared from the obtained nucleotide sequence and the genomic DNAs of 95SP and 97SE as templates. The products were separated by electrophoresis using 1% agarose gel with 100 V for 30 minutes and then visualized by ethidium bromide staining. Among the obtained amplification products, an amplification product of approximately 1.3 kb that was absent in 95SP but was present in 97SE, was subjected to TA cloning (PCR Experiment Note (PCR Jikken Note), edited and written by Taketoshi Taniguchi, YODOSHA CO., LTD. (1997)) using a pGEM T vector (produced by Promega Corporation). The nucleotide sequence was determined using ABI310 (produced by Applied Biosystems). As a result, in the DNA sequence of the amplification product, the sequence shown in SEQ ID NO: 22 was present between duplicate of 8 nucleotides. Such duplication were in the same direction and consisted of 8 nucleotides (GTTATATG) ranging from nucleotide C (nucleotide 114) and nucleotide C (nucleotide 121) in the nucleotide sequence shown in SEQ ID NO: 28. Specifically, the 8-nucleotide portion was repeated as GTTATATG . . . GTTATATG, and the sequence of SEQ ID NO: 22 were inserted between such GTTATATG and GTTATATG. Accordingly, it is clear that the non-autonomous transposon shown in SEQ ID NO: 22 is mobile. It is also clear that the transposon underwent transposition at or after the time of obtaining 97SE by mutation from 95SP.

The method for evaluating transposition by inverse PCR described here is one of effective methods for detecting mutation, in addition to a method for detecting mutation described in Example 8.

EXAMPLE 6

Evaluation of Transposase Expression by Return PCR cDNAs were prepared from the carnation clones 95SP and 97SPi by the method described in Example 3. PCR (conditions: 95° C. for 2 minutes; 30 cycles of 95° C. for 30 seconds, 56° C. for 30 seconds; and 72° C. for 3 minutes; and 72° C. for 3 minutes) was performed using primers CACTATGGATC- CTAATTCTCAAA (23 nucleotides: SEQ ID NO: 20) and GAGACTCATAGTGGTTATATACA (23 nucleotides: SEQ ID NO: 14).

PCR was similarly performed using primers TTCTTCACTTGAATTCGAACAAG (23 nucleotides: SEQ ID NO: 21) and CGCAAATACACTAAATTTATGCC (23 nucleotides: SEQ ID NO: 17). The thus-obtained amplification products were separated by electrophoresis using 1% agarose gel with 100 V for 20 minutes and then visualized by ethidium bromide staining. As a result, amplification products of predicted sizes (of approximately 1.9 kb and 1.1 kb, respectively) were detected (FIG. 5). Among the obtained amplification products, an amplification product obtained from the clone 97SPi was subjected to TA cloning (PCR Experiment Note (PCR Jikken Note), edited and written by Taketoshi Taniguchi, YODOSHA CO., LTD. (1997)) using a pGEM T vector (produced by Promega Corporation). The nucleotide sequence was partially determined using ABI310 (produced by Applied Biosystems). As a result, the nucleotide sequence was homologous to a portion of the gene encoding the transposase of the transposon of the present invention. As described above, the transcriptional expression of the transposase could be easily detected by return PCR.

EXAMPLE 7

Examination of the Presence of a Transposon in Other Plants of the Genus *Dianthus*

DNAs were prepared from carnation variety Kaly, *Dianthus chinensis* (purchased from a general flower and seed distributor), *Dianthus barbatus* (purchased from a general flower and seed distributor). DNA of 97SPi as a positive control was prepared similarly to Example 2. However, the DNA of carnation variety Kaly was prepared using the leaves of the plant grown in a greenhouse. The DNAs of the other 2 species were prepared by sowing the seeds thereof on filter paper containing water and then using cotyldons and hypocotyls after germination (on day 6 after sowing). The following PCR was performed using these DNAs as templates.

PCR (conditions: 95° C. for 2 minutes; 30 cycles of 95° C. for 30 seconds, 56° C. for 30 seconds, and 72° C. for 30 seconds; and 72° C. for 3 minutes) was performed using primers: GGTCTAGTTAGTCAGCTACGG (21 nucleotides: SEQ ID NO: 16) and CGCAAATACACTAAATTTATGCC (23 nucleotides: SEQ ID NO: 17) derived from the thus revealed nucleotide sequence of the transposon of the present invention. The amplification products were separated by electrophoresis using 1% agarose gel with 100 V for 20 minutes and then visualized by ethidium bromide staining.

As a result, similar to the case of 97SPi as a positive control, amplification products of a predicted size, approximately 460 nucleotides in length, were obtained from all of carnation variety Kaly (lane 3), *Dianthus chinensis* (lane 4), and *Dianthus barbatus* (lane 5). It was reveled that the transposon of the present invention is also present in these plants (FIG. 6).

EXAMPLE 8

Detection of Mutation

Inverse PCR described in Example 5 was performed according to Cell Engineering, Separate Volume, Plant Cell Engineering Series 2, Plant PCR Experimental Protocols (1995) 69-72. The genomic DNAs of the carnation clones 95SP and 97SPi were prepared by the method described in Example 2. The genomic DNAs of 99SP4 and 99SP5 that are bud mutants derived from the clone 97SPi and 95SP, respectively, were prepared by the method described in Example 2 as well. The DNAs were digested with a restriction enzyme Hind III or Spe I. Inverse PCR (conditions: 95° C. for 2 minutes; 30 cycles of 95° C. for 30 seconds, 56° C. for 30 seconds, and 72° C. for 5 minutes; and 72° C. for 3 minutes) was performed using these digested products as materials and primers CGAATACCGTGCTTTGGACG (20 nucleotides: SEQ ID NO: 18) and CGCAAATACACTAAATTTATGCC (23 nucleotides: SEQ ID NO: 17). The thus-obtained amplification products were separated by electrophoresis using 1% agarose gel with 50 V for 120 minutes, and then visualized by ethidium bromide staining. As a result, several kinds of amplification product could be separated each other. Furthermore, specific amplified products obtained from each of the 4 clones used herein were detected. It was thought that these results were due to the transposition of the transposon. As described above, mutation on the genomic DNAs that had been induced by the transposition of the transposon could be detected (FIG. 7).

Furthermore, the nucleotide sequences of some amplification products of inverse PCR were partially determined using ABI310 (produced by Applied Biosystems). As a result, it was confirmed that these sequences were homologous to sequences predicted to be contained in the transposon of the present invention. Accordingly, it is clear that the amplification products in this Example are target amplification products containing the transposon of the present invention.

EXAMPLE 9

Promotion of the Transposition of the Transposon Via the Environment

Excision of the transposon obtained in the present invention that is inserted into 97SPi flavonoid 3' hydroxylase can be detected through manifestation in a phenotype based on flower color change (from pink to purple). Planted 97SPi cuttings (approximately 5 cm in height) were grown according to a standard method under 2 different conditions in a greenhouse for 2 months (from Sep. 4, 2003, to Oct. 31, 2003). The presence or the absence of purple sectors was tested at the time of flowering. The first conditions consisted of a glass greenhouse, day temperature ranging from 25° C. to 33° C., night temperature ranging from 23° C. to 30° C., and natural day length ranging from 13 to 12 hours. The second conditions consisted of day temperature of 20° C., night temperature of 10° C., and day length of 8 hours adjusted by the use of a KOITOTRON artificial climate chamber (produced by KOITO MANUFACTURING CO., LTD.). As a result, whereas purple sectors were observed in 3 out of 45 flowers (6.7%) that had been developed under the first conditions, purple sectors were observed in 35 out of 51 flowers (68.6%) that had been developed under the second conditions. Accordingly, it is clear that low temperature condition, short day condition, or a combination of low-temperature and short-day condition promote the excision of the transposon to be inserted into 97SPi flavonoid 3' hydroxylase.

All publications, patents, and patent applications cited herein are incorporated herein by reference in their entirety.

INDUSTRIAL APPLICABILITY

A transposon inducing bud-mutation has been discovered for the first time through the present invention. Environmental conditions that can easily and efficiently induce bud mutation can be specified, or individual plants that easily undergo bud mutation can be selected by detecting the amount of expressed transposase by return PCR and by evaluating the methylation degree of the transposon.

Furthermore, environmental conditions that induce bud mutation can be specified or individual plants that easily undergo bud mutation can be selected by detecting the transposition of the transposon according to the technique described in description concerning the methods for detecting mutation.

The use of the thus-obtained environmental conditions and individual plants enable efficient induction of bud mutation. Moreover, the use of a transposase gene of the transposon in a manner involving genetic engineering enables efficient production of bud mutants. As described above, an ideal mutation method is provided, which is characterized by mutation at high frequency despite a small number of mutation positions per cell, and which addresses problems associated with conventional techniques. Thus, advancement in the efficient breeding of orchards, flowers and ornamental plants, and the like, for which mutation breeding is important, becomes possible.

Furthermore, when plants show mutability (which is a problem in terms of agricultural production) due to a transposon, stabilization becomes possible via promotion of the transposition of the transposon. Moreover, it becomes possible to perform stable agricultural production by avoiding environmental conditions that easily induce transposition, or by suppressing the expression of a transposase gene in a manner involving genetic engineering.

It becomes possible to easily identify and isolate a gene that causes mutation from the obtained bud mutants. It also becomes possible to easily detect (select) mutants wherein the relevant transposon has been inserted into a target gene by a technique such as PCR. Thus, mutants wherein gene expression has been suppressed can be efficiently obtained. Such technology can accelerate molecular genetic studies in plant.

The invention claimed is:

1. An isolated DNA sequence comprising
(A) the nucleotide sequence of SEQ ID NO: 4; or
(B) nucleotides 1056 to 3497 of SEQ ID NO:4.

2. A method for inducing bud mutation in a plant comprising transforming the plant with the nucleotide sequence of SEQ ID NO:4 wherein expression of the transposase encoded by SEQ ID NO:4 induces transposition of the transformed DNA wherein said transposition induces bud mutation in the plant.

3. The method of claim 2, wherein the expression is induced by exposing the transformed plant to low temperature.

4. The method of claim 2, wherein the expression is induced by exposing the transformed plant to a shortened day.

5. The method of claim 2, wherein the expression is induced by exposing the transformed plant to low temperature and a shortened day.

* * * * *

UNITED STATES PATENT AND TRADEMARK OFFICE
CERTIFICATE OF CORRECTION

PATENT NO. : 7,638,298 B2  Page 1 of 1
APPLICATION NO. : 10/571779
DATED : December 29, 2009
INVENTOR(S) : Momose et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 588 days.

Signed and Sealed this

Ninth Day of November, 2010

David J. Kappos
*Director of the United States Patent and Trademark Office*

SEQUENCE LISTING

```
<160> NUMBER OF SEQ ID NOS: 39

<210> SEQ ID NO 1
<211> LENGTH: 13
<212> TYPE: DNA
<213> ORGANISM: Dianthus caryophyllus

<400> SEQUENCE: 1
tagagctggc aaa                                                    13

<210> SEQ ID NO 2
<211> LENGTH: 13
<212> TYPE: DNA
<213> ORGANISM: Dianthus caryophyllus

<400> SEQUENCE: 2
tttgccagct cta                                                    13

<210> SEQ ID NO 3
<211> LENGTH: 814
<212> TYPE: PRT
<213> ORGANISM: Dianthus caryophyllus

<400> SEQUENCE: 3

Met Asp Pro Asn Ser Gln Asn Pro Tyr Asn Ser Lys Arg Pro Arg Gly
 1               5                  10                  15

Thr Thr Ser Thr Gln Pro Glu Ser Pro Thr Pro Val Thr Pro Pro Ser
            20                  25                  30

Gln Pro Phe Asn Met Asn Gln Trp Ala Gly Phe Thr Pro Ser Glu Leu
        35                  40                  45

Gln Asn Asn Leu Trp Ser Asn Gln Asn Pro Thr Pro Phe Gly Val Asn
    50                  55                  60

Pro Thr Asn Leu Phe Ser Asn Pro Thr Ile Phe Glu Asn Val Pro Asp
65                  70                  75                  80

Met Ser Gln Phe Thr Ser Pro Tyr Pro Pro Phe Asp Gln Pro Ile Arg
                85                  90                  95

Pro His Ala Ile Arg Pro Gln Pro Met Phe Pro Phe Ser Asn Pro Asn
            100                 105                 110

Gln Phe Ser Gln Arg Ser Gln Glu Gly Ser Ser Thr Tyr Ser Gln Pro
```

```
                115                 120                 125
Glu Ser Ser Thr Gln Pro Glu Ser Ser Gln Pro Glu Ser Ser Thr
    130                 135                 140
His Thr Thr Asp Thr Gln Pro Asp Pro Thr Gln Pro Leu Pro Pro Asn
145                 150                 155                 160
Asn Thr Asp Ile Trp Met Thr Glu Pro Glu Met Leu Lys Val Ile Ser
                165                 170                 175
Arg Lys Asn Ser Ser Val Ala Trp Pro His Tyr Ile Leu Thr Thr Asp
                180                 185                 190
Lys Lys Lys Ala Lys Cys Arg Tyr Cys Asn Thr Ile Tyr Thr Ala Lys
                195                 200                 205
Ser Gln Asn Gly Thr Gly His Leu Ile Arg His Ile Thr Lys Lys Cys
    210                 215                 220
Thr Ala Met Pro Gln Ala Gly Gln Ser Thr Met Asp Asp Phe Leu Thr
225                 230                 235                 240
Lys Pro Asn Ala Pro Glu Gln Tyr Lys Tyr Asp Tyr Asp Glu Cys Ser
                245                 250                 255
Ala Glu Leu Ser Lys Met Ile Ile Gln Thr Glu Glu Pro Phe Leu Leu
                260                 265                 270
Ala Glu Arg Asn Ala Phe Asn Arg Tyr Val Lys Lys Asn Gln Pro Glu
                275                 280                 285
His Lys Pro Thr Gly Arg Arg Val Arg Ser Asn Ala Met Gln Gln
    290                 295                 300
Tyr Cys Thr Leu Lys His Lys Leu Ile Ala Asp Phe Glu Asn Met Ser
305                 310                 315                 320
Cys Lys Phe Asn Leu Thr Ala Asp Val Trp Asp Ser Gly Val Asp Tyr
                325                 330                 335
His Tyr Leu Cys Ile Thr Ala His Trp Val Asp Arg Glu Trp Asn Leu
                340                 345                 350
Gln Lys Arg Ile Ile Ser Phe Ser Lys Leu Glu Phe Pro His Asn Ala
                355                 360                 365
Ile Asn Met His Asn Ile Ile Met Ala Ser Ile Asn Glu Tyr Asn Ile
    370                 375                 380
Lys Ser Lys Ile Leu Thr Val Thr Phe Asp Asn Ala Thr Ser Met Thr
385                 390                 395                 400
Ala Val Ala Asn Met Leu Lys Asn Ser Leu Glu Ser Val Leu Leu Asn
                405                 410                 415
Gly Asp Leu Leu His Val Arg Cys Ala Cys His Val Leu Asn Leu Cys
                420                 425                 430
Val Arg Asp Gly Leu Glu Gly Leu Lys Gln Tyr His Ser Thr Phe Lys
                435                 440                 445
His Val Val Leu His Leu Asn Ser Asn Lys Ser Arg Arg Gln Glu Trp
    450                 455                 460
Arg Asn Tyr Cys Lys Ser Val Gly Val Lys Tyr Arg Lys Phe Pro Met
465                 470                 475                 480
Glu Asn Asn Thr Arg Trp Asn Ser Met Tyr Ile Met Leu Ser Ala Cys
                485                 490                 495
Ile Glu Tyr Lys Gln Pro Leu Thr Ala Phe Trp Asn Gly Ile Phe Pro
                500                 505                 510
Asp Ser Pro Ile Leu Glu Asn His Trp Asn Asn Met Glu Met Tyr Val
                515                 520                 525
Asp Phe Leu Cys Ala Phe Met Asp Ala Thr Lys Ser Phe Ser His Val
                530                 535                 540
```

-continued

Tyr Lys Thr Thr Ala Pro Tyr Phe Leu Gly Asn Ile Ile Pro Ile Ala
545                 550                 555                 560

Glu Leu Phe Gln Lys Tyr Arg Ala Gln Gln Ser Tyr Leu Gly Phe Leu
            565                 570                 575

Pro Lys Met Glu Glu Lys Phe Leu Lys Tyr Trp Thr Asp Ile Pro Tyr
        580                 585                 590

Val Tyr Val Phe Ala Val Ile Leu Asp Pro Arg Trp Lys Phe Asp Gly
    595                 600                 605

Ala Ile Ser Leu Val Thr Ile Tyr Lys Gln Leu Met Asn Ile Asp Phe
610                 615                 620

Asp Pro Asp Leu Tyr Lys Asp Glu Ile Arg Gln Ala Phe Phe Asn Val
625                 630                 635                 640

Tyr Asn His Tyr Glu Ser Arg Ile Gly Pro Ser Thr Arg Pro Pro Ser
            645                 650                 655

Arg Ala Gly Ser Ser Gly Ala Gly Gly Ser Arg Ala Phe Ala Gly Ala
        660                 665                 670

Thr Leu Asn Lys Leu Lys Gly Leu Val Ser Gln Leu Arg Pro Asp Val
    675                 680                 685

Ala Gln Ser Thr Ser Thr Thr Ser Asp Leu Ala Glu Tyr His Met Tyr
690                 695                 700

Ile Asn Tyr Asp Tyr Leu Arg Ser Phe Thr Asp Glu Ala Asn Val
705                 710                 715                 720

Leu Asp Leu Leu Leu Trp Trp Lys Gly Gln Arg Arg Gln Leu Pro Val
            725                 730                 735

Met Ser Ala Met Ala Gln Asp Phe Leu Ser Ile Gln Val Ser Ser Val
        740                 745                 750

Ala Ser Glu Arg Ala Phe Ser Ala Ser Lys Arg Val Leu Asp Glu Lys
    755                 760                 765

Arg Thr Ser Leu Arg Ser Asp Thr Leu Glu Met Cys Val Cys Tyr Lys
770                 775                 780

Asp Trp Met Asp Ala Glu Glu Arg Thr Gln Gly Met Glu Asn Glu Glu
785                 790                 795                 800

Asp Glu Asn Ser Asp Asp Glu Thr Ser Thr Glu Ser Asn Ala
            805                 810

<210> SEQ ID NO 4
<211> LENGTH: 4274
<212> TYPE: DNA
<213> ORGANISM: Dianthus caryophyllus

<400> SEQUENCE: 4
tagagctggc aaaccggtgc acggcacgac gggcggcccg aattcggccc ggtttggcac      60
gggcccggta cggccggtt ttgggtttcg gctggcccg agcacggccc gacgtgctaa      120
atgcgtgttt cgtaaaaaaa aaaaaaaaa ataaggaata tggcccggcc cgaaccgaaa      180
cccggttttg ggcccgattt gggcccggtt ttgcacgga ttgggcacgg cacggtttgc      240
acgaattggg cccgaatttt ggtatgcaat agagctggca cgaattgggc cgaattttg      300 gtgtgcaact tcaagtcttc aacggcactt ttttttttt ggcctgcaac ttgccaactt      360
gcctagttgc ctcttcattc aacgacattt ttgcttattt tttttgcttc aacggcattt      420
ttgcttcaac ggcatttttg cttatttta ttttattttt ttatttttt aattctaatt      480 tattttctat aaataccat aatttcaatt cattttccac aactcaattc aactcttctt      540
ctcaatttct catctacaat tttcaactta atcttatatt cttacaaaaa aaatatacct      600

```
taaaaatatt atataaaatt attaatacta aattattta gtaatataaa aaaaaattgt    660
gttactcata ataatcgggt ttacaaaatt ggtggagttt acgccttgtc ttcgaatttt    720
acaattcgtc atccaaatat ccaaatactc ctatagcttt gtttgcaatt tctaacttta    780
tactccgtat ttatttattt gcataattag tttaattatt tatttgctag attagttaaa    840
ttactccgta tttactttca tattcactac ttagtaatca ctacttagta atcactaaat    900
ctatctttgt ttaattatct ttgtttaatt agttaagtta tttacttgca tactaaatta    960
ttttagcaat ataaaaaaaa aaaaaatcta cctttgttta attatctact ttcatattca   1020
ctaattagtc actaaatcac taatcactaa tcactatgga tcctaattct caaaaccctt   1080
ataattctaa gagaccacgt ggtacgactt cgacccaacc ggaatcaccc actcccgtaa   1140
caccaccaag tcaaccattt aacatgaacc aatgggcggg ttttactcct tcagagttac   1200
aaaataattt gtggtcaaat caaaatccga ctcctttcgg tgttaatcct acaaatctat   1260
tttcgaatcc gacaattttt gaaaatgtac ccgacatgag tcaatttaca agtccttacc   1320
caccgttcga ccaaccaatt agaccacatg ctatcagacc tcaaccaatg tttccatttt   1380
cgaatccaaa tcaattttca caacggtcac aagaagggtc ttccacttac tcacaacccg   1440
agagctcgac ccaacctgaa tcctccagcc aacctgaatc ctcaacccat actactgaca   1500
cacagcctga tccaacacaa cctttacccc ccaataatac cgatatatgg atgaccgaac   1560
ctgaaatgtt aaaagtaata agtagaaaaa actctagtgt tgcatggcca cattatatct   1620
taaccacaga caaaaaaaaa gctaagtgta gatattgtaa cacaatatac acagctaagt   1680
cgcaaaatgg caccggtcac ctaattagac ataactaa aaaatgtaca gcaatgcctc     1740
aagctgggca aagtacaatg gatgactttt tgacaaaacc caatgcccct gaacaatata   1800
aatatgatta tgatgaatgt agcgcagaat tgtctaaaat gattatccaa acagaagaac   1860
cattttact tgcggaacgt aatgcattta acagatatgt taaaaagaac caaccagagc    1920
ataaacctac gggtagaaga agagttagaa gtaatgcaat gcaacaatat tgtacattaa   1980
aacataaatt aattgccgat tttgaaaaca tgtcatgtaa atttaactta actgctgatg   2040
tatgggattc tggtgttgat taccattatt tatgtattac cgctcattgg gtagatcgtg   2100
agtggaattt acaaaaacga attatttctt tttctaaatt agaatttcca cataacgcta   2160
ttaacatgca taacattatt atggccagca ttaatgaata ataatattaaa tctaaaatat   2220
taaccgtcac ttttgataat gcaacgagta tgaccgctgt ggctaatatg ttgaaaaata   2280
gcttagaatc tgtattattg aatggtgatt tgttgcatgt gagatgtgct tgtcatgttt   2340
taaacttatg tgttagagac ggtcttgaag gtcttaagca atatcattca acttttaaac   2400
atgttgttct tcacttgaat tcgaacaagt cgagacgtca agaatggcga aattattgta   2460
aatctgtagg tgttaagtat agaaaatttc caatggaaaa taacactagg tggaattcta   2520
tgtatattat gttatctgct tgtattgagt ataaacaacc tcttactgca ttttggaatg   2580
gtatttttcc tgatagtcca atacttgaga accattggaa caatatggag atgtatgttg   2640
atttttgtg tgcttttatg gatgccacta aatcttttc acatgtatat aaaaccaccg     2700
ccccttattt tcttggtaac attattccca ttgccgaact ttttcaaaaa taccgtgctc   2760
aacagtctta ccttgggttt cttcccaaaa tggaggaaaa gtttctcaaa tattggacgg   2820
atattcctta tgtttatgtt tttgctgtta ttttagaccc taggtggaaa tttgacggag   2880
ctatatcgtt agttactatt tataaacaat taatgaacat agattttgat ccggatttgt   2940
```

```
ataaagatga aattagacaa gcttttttta atgtatataa ccactatgag tctcgtattg    3000
gtccctcaac tcgtccacct tcccgtgcag gttccagtgg tgctggtggt agtagagctt    3060
ttgcaggagc caccettaac aaacttaagg gtctagttag tcagctacgg ccggatgtag    3120
cacaatctac tagtactaca tccgacttgg ccgagtatca tatgtatatt aactacgatt    3180
atcttcgttc ttttacagat gaggaggcaa acgtgttgga tcttttgctt tggtggaaag    3240
gacaacgtag acaacttcca gtgatgtctg caatggcgca agacttttta agcattcaag    3300
tatcctcagt tgcatctgaa agggcattta gtgcatctaa acgggtgttg gacgaaaaaa    3360
gaactagttt gagatcagat acacttgaaa tgtgtgtgtg ctacaaagat tggatggatg    3420
ccgaagaaag aacgcaaggg atggagaacg aagaagacga gaatagcgac gacgaaacta    3480
gtaccgaatc caacgcttaa taaatttgta atatttgtac aataaagacg gcataaattt    3540
agtgtatttg cgttttcaat aattttaata gaatttttag tgctttctca ataatttttat    3600 aaatttctaa ttttaataat tttaatagaa tttaatatta ctctttcgtc gctacttatt    3660 cttttatga gtttatataa aaattcaatt acataatagt atataaagat tcaaaaccta    3720
aattataata ataaaaacta acctttaatt aaaaaaacta acttataatt aaaaaaacta    3780
aaactccaaa ataccaaaa taaacatcaa ataaaaaaaa aactaacctt taattaaaaa    3840
aactaactta taattaaaaa aactaactta taattaaaaa aactacaact ccaaaaatac    3900
caaaataaac atcaaaaaaa aaaaaaaaaa aaaagaaaa aagagaagt cagtgaagta    3960 tgtgcacgtg cacagtgcac caaaaacaca acaccaata cccatgtgct aaaactaaaa    4020
aaaaaataaa aaatcagtga aaatttggca ggcccgaaat tggcccgatt ttggcccgaa    4080
cacggcccgg cacggcccga atttggcacg aattcttccg tgctccaaac gtgcctcgga    4140
ttaacaaaaa aaaattggca cggcccgagc acggcccgaa agcacgaata ccgtgctttg    4200
gacgggccaa atttattct aggcacgacg ggccggcccg aagcacggca cggcccgttt    4260
ttttgccagc tcta                                                      4274

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)
<223> OTHER INFORMATION: a, c, g, t, unknown or other
<220> FEATURE:
<221> NAME/KEY: modified_base
<222> LOCATION: (24)
<223> OTHER INFORMATION: a, c, g, t, unknown or other

<400> SEQUENCE: 5
aagcatattg cntayaayta ycanga                                         26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)
<223> OTHER INFORMATION: a, c, g, t, unknown or other
```

```
<220> FEATURE:
<221> NAME/KEY: modified_base
<222> LOCATION: (21)
<223> OTHER INFORMATION: a, c, g, t, unknown or other

<400> SEQUENCE: 6
ccatctcttg cdatngccca nayrtt                                          26

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taaacgggta ccacattccc a                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aagtcggaaa acctctttga t                                               21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agcaggaaca aagccagtac a                                               21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gttaacaatt caatactcag taca                                            24

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aatgtcaccc ttagaggtaa ctttcta                                         27

<210> SEQ ID NO 12
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 12
tagcaaggcc ttaatttctg tg                                                  22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cacacgattc gtttgcgacc                                                     20

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gagactcata gtggttatat aca                                                 23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
taacaacacg taaccgaaaa tata                                                24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtctagtta gtcagctacg g                                                   21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgcaaataca ctaaatttat gcc                                                 23

<210> SEQ ID NO 18
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 18
cgaataccgt gctttggacg                                               20

<210> SEQ ID NO 19
<211> LENGTH: 5743
<212> TYPE: DNA
<213> ORGANISM: Dianthus caryophyllus

<400> SEQUENCE: 19

| | | |
|---|---|---|
| aatgtcaccc ttagaggtaa ctttctacac catagcccta gccacaatcc tctactacct | 60 |
| catccccacc gtcttccgcg gccaccaaaa accgcttcct ccagggccac gaccatggcc | 120 |
| catcgtggga aacctaccac atatgggcca ggcaccgcac cagggcttag cagccctggc | 180 |
| gcagaagtat ggccctctat tgtatatgag actggggtac gtggacgttg ttgtggccgc | 240 |
| ctcagcgtct gtggcgaccc agtttcttaa gacacatgac ctaaattttt cgagtaggcc | 300 |
| accgaattcg ggggctaaac acattgctta taactatcaa gaccttgttt ttgcacctta | 360 |
| tggacctaaa tggcgcatgc ttaggaaaat ttgttcctta cacatgtttt cttctaaggc | 420 |
| tttggacgat tttagacttg tccgtcaggt ttgttctttg acgacgtaaa tttactaact | 480 |
| ttatggccac aaattcttta gtaagacggt gtcaatataa tgttattata atacctctca | 540 |
| tataaattac tttagtaatt actaagttat ttgagtgatt tcttaaaaa ttagcagatt | 600 |
| tcacgttata aaactgtctt acaggaaaca tagtactctg tattttataa tttgttatac | 660 |
| tacatgtgca tggtataatt aaaaagttgt cacgtgccac gtgggtagat tatcatcttt | 720 |
| gtttagtgat cactaataaa tctcatgatt ttaatgatat cggatttaaa aagcgacgtt | 780 |
| tatttgattg taaaaaatga aacaagaaaa taaagatta aaagtacaaa catatataag | 840 |
| gtgtgtcaag gggaacttat tatagttcat gcaggttcaa ttcaccgtca caaataaaca | 900 |
| accataactt gttgttggat taaaacaaat ccgagtgcaa gttttttaaat tttaatactc | 960 |
| cgaatatgat atgatatgat atgatatgat atgatatgtt acgagtttat tttcgtttga | 1020 |
| atgacgctta taatatacaa gtcatttatc aaacttaggc cctgttttta tcgtcttttt | 1080 |
| ggagctgaac taaactaagc taaacttata aaaaatagat ttatatgagc tgaaattata | 1140 |
| ggtagctgaa gtcatttaa tttaaagctt agtagggctt ataggagctg aacttattag | 1200 |
| agctgaactt ataggagctg aactgaactt ataagagttg agctgaatta taagaactga | 1260 |
| cattaaactg aaaagaacag ggccttagtt ttctcaattt aatttattaa atcaaaatta | 1320 |
| tatatattta tataaataaa agattcaatt tactcttata ctttatatag aagtgataga | 1380 |
| gagattccac agagtagatg aaaacgatac tttttatatg gaataatata tatattcaaa | 1440 |
| tagcatttgc aggattttat aaataatgta ataaatccat aaatttcttg aatgctgctt | 1500 |
| ttagttaatt aaaaatcatt acattgattt ttctacttta tttggtccct tgttaatttt | 1560 |
| catcaatgat acatttgtaa tccgtgactg acctactatt ttggtccgta gtacaatttt | 1620 |
| aactcaaaga catataaatc tgctaaaaat caattaagac gataaacaaa caaatttaca | 1680 |
| aagaaaaaaa caatgttatc atatattcca atagttgaat tcgtttgttt attatttatt | 1740 |
| tcgtaatgag ctagcgtaga tcaactattt tctaaattgg aatataaatt gatcacataa | 1800 |
| tcataacata aaatcattag ctaggaaatg tcaagtattt aatttatgat catttccaag | 1860 |
| attaaaaagt aaaaaaatga ttaaaatgca aaaaagttca cagtaacatt ataaagttta | 1920 |

```
acataaaaat aaacacctta caaaactaat tgatattatt tcaactgtct acgttgtcac   1980
ataaatgaga gtatttacgt ctaactaatt gatatttcaa ctgtttgatt gactttactt   2040
taaaattggg aataaaattt ctttgttatc cattgaattt taagctcata aattttgaat   2100
aatagactaa tagagtaata atcaataatt tgtcaatggt tgattgggta ggtaataaac   2160
aggtgccaat tttatgcccg tgcaaattgc acgggtaagt ttttttttata aaatttaagt   2220 agctacaatt ttagttaaac gtaagacttt aagagtactt atgtacttat gtggttaggg   2280
gtcgtagtta atcatcaatt gtaaccaatt gtttataact aattttaact atttcatact   2340
cgataatatt ggacgattaa tcattaatta acttaagcac gataatttga atttgtttga   2400
aaaaaaaaag acgcgtgaat aatcattcga tcttttgtta cactaaaact atatacagga   2460
agaagtgtct atactggtaa acgcgatagc aaaagcagga acaaagccag tacaactagg   2520
acaactacta ctcaacgtgt gcaccacaaa tgccttatcg agggtgatgc tagggaagcg   2580
agttctcggt gatggcacag ggaaaagcga cccaaaagcc gaggaattta aggacatggt   2640
gctggagtta atggttctca ccggagtttt taacattggc gattttgtac cggcattgga   2700
atgtctagac ttacaaggtg ttgcatctaa atgaagaaa ttacataaaa gacttgataa   2760
ttttatgagt aacattttgg aggaacacaa gagtgttgca catcaacaaa atggtggaga   2820
tttgctaagc actttgatat cttttgaagga taattgtgat ggtgaaggtg gcaagtttag   2880
tgacacagaa attaaggcct tgctattggt aatgtttctt attattctac gatttacgca   2940
gtttcgattc agtcatttct tattaatttt agtcagattt aaccttttt gaaaaaaaaa   3000 atatattatg aaagtggtta gattcaattc accggccttc tatttaaatt taatgagtaa   3060
aataattaat ccaattaata actatataaa tccgaaagta tgtattgtga aataacttgc   3120
ttattaattt taatgtagaa aaaacaagtt aaattaaatt gaattacatt gaacgaaaaa   3180
gatagaataa aggggaaata tcctcaattt atactccgta ttagttatgt tgcttgaaaa   3240
tgaggcaaag gtagataggt cataaattat atactcggat ccgtataagt gaaaaattac   3300
actaggccac ttattattac atactccata ttaattattt tttaattata catttagttt   3360
ataattttaa ctgaacgtaa attaaaataa tttactccgt atcaaataca caacgatccg   3420
tatttaacat atacgaaatt ggtagagtac gtatcaaatg atgaaatcaa caagaaaaac   3480
cctacgcaat taaaatactt accaaaatgt ggtagctaca actttcagta gtacaactat   3540
ttgaatggag gatcaagtgt gtgttgcaca tgcatgatta ttgtgtacgt tggacaatgc   3600
tacactaaat ttatttattt ttcaattaga gttaaattta tcggagctaa atttattaaa   3660
tttgaggtaa atttattacg gagtagattt gagttcatct gtgcataaat atttaatctg   3720
attgtctcag tagagctgaa ttaagccaaa ataacatact ttgttttact ttacatttgt   3780
tctccctgtc tcaaaagtaa atatatacag tcaaataaaa taaaagtagt acggagtatt   3840
aaatatttag cacgaagtat ataatttta acaacacgta accgaaaata tagacacata   3900
agttaattac gttaagtcct ccctaaaata ataataattc tccacctacc attcttccaa   3960
cttcttttat tgcctgacgt tctacaaatc aataactatt caaaccctac ctacgaatca   4020
catatatttt gtgttattaa taattttgt cgtctttatt taggaccttt tttttttttt   4080
ttttgaatat gacgtgctaa atagtaaata ctctgtactt catatgaaaa tacattaatt   4140
aattggttac ggagtactcc ctcccatttg gaatgatctt cccttacgtt aatgtggcaa   4200
attaattgcc atatcagagc ccgtgattca ccagcccgtt tgatatttag ggcactactt   4260
gtgttgtcta tttcacattt attgtagtgt gttatactcc gtattattca tcatttacat   4320
```

-continued

```
aattacatac ggagtattat tctttctttt atgtatttcc tgttaattta tcttacaacg    4380
ttaaacatga ataaaatgta ctgagtattg aattgttaac tgtgaataac aatgaatgtt    4440
ggcgagttaa catattaaat tattactctc tctatttcat cagattagcc ccattggttc    4500 acttttttgtg aggaaaaaaa tgagaccata gagtaaattt tatcgaagaa atacaacaaa    4560
taacatgatt cccttaaaat acaggattta tttacagctg aacagacac atcatctagt    4620 acaactgaat gggccatagc cgaactaatt cgccatccaa aaatcttagc ccaagttcaa    4680
caagaaatgg actcagtcgt gggccgagac cgactcatag ccgaagctga cataccgaac    4740
ctaacctact tccaagccgt aatcaaagag gttttccgac ttcacccgtc caccccgctt    4800
tccctaccac gggtcgcaaa cgaatcgtgt gaaataaacg ggtaccacat tcccaaaaaa    4860
caccacttta ttggtgaatg tgtgggccat cgcacgcgac cctgaggttt gggccgaccc    4920
gttagagttt aaacccgaaa gattttttgcc gggcggcgag aagcccaatg tggatgtgaa    4980
aggaaacgat tttgagctga ttccgttcgg ggcgggccga cggatttgtg ctgggctgag    5040
tttgggcctg cgtatggtcc agttgatgac agccactttg gcccatacct atgattgggc    5100
tttagctgat gggcttatgc ccgaaaagct taacatggaa gaggcttatg ggcttacgtt    5160
acagcgtaag gtgccactaa tggtccaccc gacccgtcgg ctctcggccc acgtttataa    5220
ttcggggttt taaagtgggc actttgttg tgtattattc cgtactagtt tgaaaaataa    5280
cgtatcagag aaaatgttcg ttatgacaat atcgttatgt attttgtata atgtgaggca    5340
ttagaccagt ataatatggt taattatatg ttcaattgaa ctattttact tttatgtat    5400 tttagggtaa ttttattttt gaaactacgt actccgtatt ttagaataat taggacatgt    5460
tgatgtgcat ctaagggtcg ttaatctagt agtttcgttt tttcctttct cttttatgga    5520
cagttgatat aaaataaaat tcattttatg tcccttcttt tggttgaaaa ataagctact    5580
gtttacgcta ctttgtggtt ttcgatacaa aaatgttgat gacaaattgc cttgtatcgg    5640
ttttcacatt aaaattattt tctaaagttt tatgttaacg aaaaattata acattaagag    5700
tttagttcga ttttaaaaac tccaaaaatt accgctacat atg                      5743
```

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cactatggat cctaattctc aaa                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttcttcactt gaattcgaac aag                                              23

<210> SEQ ID NO 22
<211> LENGTH: 732
<212> TYPE: DNA

<213> ORGANISM: Dianthus caryophyllus

<400> SEQUENCE: 22

```
tagagctggc aaaccggtgc acggcccgac gggcggcccg aatccggccc ggtttggcac      60
gggcccgata cggcccgatt tggatattcg ggttggcacg agcacggccc gacgtgcaaa     120
atgcgtgctt cggcaaaaaa aaaaaaaaaa taaggaattg gcccggcccg gatcgaaacc     180
cggatttggg cccgttttgg gcacggtttg ggcccggtat ggcacggccc gtttgggcac     240
ggattgggct ggccttttcaa aaactcctcc cattctcctg caagttaacg gctagtttca    300
tttttttttt tttttttttt ttttggtcc ttcactcagt cactcacatt cactccttct      360
ctttccaagt tccaagtact tgagtacttc caagttccaa caatccaact tgagtacttg     420
agtactcaca ttcactcctt ctctttccaa ataccgaaaa aaaaagaaa aaaaaaaaa       480
aaaaaaaat tcaatgaaaa tttcggccgg cccgaatttg gcccgaacac ggcccgggcc      540
cggcccggta cggcccgaat ttggcacgaa ttttaccgtg ctcaaaacgt gcctcggatc     600
aacaaaaaaa aaatggcccg gcccgagcac ggcccgaaag cacgaatacc gtgctttgga    660
cgggcctaat ttttggttgg gcacgacggg ccggcccgaa gcacggcacg gcccgttttt    720
ttgccagctc ta                                                         732
```

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
agatctagag ctggcaaacc ggtgc                                            25
```

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

```
agatctagag ctggcaaaaa aacgggc                                          27
```

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

```
tcgtgccgtg caccggttt                                                   19
```

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tatacggagt accacaatca ga                                              22

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctagtatgct agtctgaagg c                                               21

<210> SEQ ID NO 28
<211> LENGTH: 462
<212> TYPE: DNA
<213> ORGANISM: Dianthus caryophyllus

<400> SEQUENCE: 28
tatacggagt accacaatca gaatatataa caaacaaaaa acatattaag cacagcacat     60
acgtcataaa cctatggcat gtaaaaggtc ttctaagttc taacaaggga gtacatataa    120
ccacgggcaa aatcaacagt tccacgtgat tcttcattaa gccaaataga agtgaggatg    180
agtgtgtaca aaaagccgtg gaagagtact tcactcccat ggcaatatgc attccctcta    240
acaagcactg atacaacacg ataaaccaag ctacaattta ccacggtgaa gtcgaaacat    300
ggccaattga gatgcagatt ttcctcatcc aacatcacgg ataataggct cctactagtc    360
cgcggtcagc aaccaatgca ccctcatttt acccagaata tggcataagc attcatcttt    420
tagctaacaa cagcctcaat ggccttcaga ctagcatact ag                       462

<210> SEQ ID NO 29
<211> LENGTH: 11
<212> TYPE: DNA
<213> ORGANISM: Zea mays

<400> SEQUENCE: 29
tagggatgaa a                                                          11

<210> SEQ ID NO 30
<211> LENGTH: 12
<212> TYPE: DNA
<213> ORGANISM: Antirrhinum majus

<400> SEQUENCE: 30
taaagatgtg aa                                                         12

<210> SEQ ID NO 31
<211> LENGTH: 14
<212> TYPE: DNA
<213> ORGANISM: Arabidopsis thaliana

<400> SEQUENCE: 31 tagggtgtc aaaa                                                        14

<210> SEQ ID NO 32
<211> LENGTH: 10
<212> TYPE: DNA
<213> ORGANISM: Arabidopsis thaliana

<400> SEQUENCE: 32
tagggatgtt                                                            10

<210> SEQ ID NO 33
<211> LENGTH: 12
<212> TYPE: DNA
<213> ORGANISM: Arabidopsis thaliana

<400> SEQUENCE: 33
tagaagtgtc aa                                                                12

<210> SEQ ID NO 34
<211> LENGTH: 12
<212> TYPE: DNA
<213> ORGANISM: Arabidopsis thaliana

<400> SEQUENCE: 34 tagggtgtc aa                                                                 12

<210> SEQ ID NO 35
<211> LENGTH: 14
<212> TYPE: DNA
<213> ORGANISM: Arabidopsis thaliana

<400> SEQUENCE: 35 tagggggtc aaaa                                                               14

<210> SEQ ID NO 36
<211> LENGTH: 592
<212> TYPE: PRT
<213> ORGANISM: Dianthus caryophyllus
<220> FEATURE:
<221> NAME/KEY: MOD_RES
<222> LOCATION: (480)..(496)
<223> OTHER INFORMATION: variable amino acid

<400> SEQUENCE: 36

Arg Lys Asn Ser Ser Val Ala Trp Pro His Tyr Ile Leu Thr Thr Asp
  1               5                  10                  15

Lys Lys Lys Ala Lys Cys Arg Tyr Cys Asn Thr Ile Tyr Thr Ala Lys
             20                  25                  30

Ser Gln Asn Gly Thr Gly His Leu Ile Arg His Ile Thr Lys Lys Cys
         35                  40                  45

Thr Ala Met Pro Gln Ala Gly Gln Ser Thr Met Asp Asp Phe Leu Thr
     50                  55                  60

Lys Pro Asn Ala Pro Glu Gln Tyr Lys Tyr Asp Tyr Asp Glu Cys Ser
 65                  70                  75                  80

Ala Glu Leu Ser Lys Met Ile Ile Gln Thr Glu Glu Pro Phe Leu Leu
                 85                  90                  95

Ala Glu Arg Asn Ala Phe Asn Arg Tyr Val Lys Lys Asn Gln Pro Glu
            100                 105                 110

His Lys Pro Thr Gly Arg Arg Val Arg Ser Asn Ala Met Gln Gln
        115                 120                 125

Tyr Cys Thr Leu Lys His Lys Leu Ile Ala Asp Phe Glu Asn Met Ser
    130                 135                 140

Cys Lys Phe Asn Leu Thr Ala Asp Val Trp Asp Ser Gly Val Asp Tyr
145                 150                 155                 160

His Tyr Leu Cys Ile Thr Ala His Trp Val Asp Arg Glu Trp Asn Leu
                165                 170                 175

Gln Lys Arg Ile Ile Ser Phe Ser Lys Leu Glu Phe Pro His Asn Ala
            180                 185                 190

```
Ile Asn Met His Asn Ile Ile Met Ala Ser Ile Asn Glu Tyr Asn Ile
            195                 200                 205

Lys Ser Lys Ile Leu Thr Val Thr Phe Asp Asn Ala Thr Ser Met Thr
        210                 215                 220

Ala Val Ala Asn Met Leu Lys Asn Ser Leu Glu Ser Val Leu Leu Asn
225                 230                 235                 240

Gly Asp Leu Leu His Val Arg Cys Ala Cys His Val Leu Asn Leu Cys
                245                 250                 255

Val Arg Asp Gly Leu Glu Gly Leu Lys Gln Tyr His Ser Thr Phe Lys
            260                 265                 270

His Val Leu His Leu Asn Ser Asn Lys Ser Arg Arg Gln Glu Trp
        275                 280                 285

Arg Asn Tyr Cys Lys Ser Val Gly Val Lys Tyr Arg Lys Phe Pro Met
        290                 295                 300

Glu Asn Asn Thr Arg Trp Asn Ser Met Tyr Ile Met Leu Ser Ala Cys
305                 310                 315                 320

Ile Glu Tyr Lys Gln Pro Leu Thr Ala Phe Trp Asn Gly Ile Phe Pro
                325                 330                 335

Asp Ser Pro Ile Leu Glu Asn His Trp Asn Asn Met Glu Met Tyr Val
            340                 345                 350

Asp Phe Leu Cys Ala Phe Met Asp Ala Thr Lys Ser Phe Ser His Val
        355                 360                 365

Tyr Lys Thr Thr Ala Pro Tyr Phe Leu Gly Asn Ile Ile Pro Ile Ala
        370                 375                 380

Glu Leu Phe Gln Lys Tyr Arg Ala Gln Gln Ser Tyr Leu Gly Phe Leu
385                 390                 395                 400

Pro Lys Met Glu Glu Lys Phe Leu Lys Tyr Trp Thr Asp Ile Pro Tyr
                405                 410                 415

Val Tyr Val Phe Ala Val Ile Leu Asp Pro Arg Trp Lys Phe Asp Gly
            420                 425                 430

Ala Ile Ser Leu Val Thr Ile Tyr Lys Gln Leu Met Asn Ile Asp Phe
        435                 440                 445

Asp Pro Asp Leu Tyr Lys Asp Glu Ile Arg Gln Ala Phe Phe Asn Val
        450                 455                 460

Tyr Asn His Tyr Glu Ser Arg Ile Gly Pro Ser Thr Arg Pro Xaa
465                 470                 475                 480

Xaa Xaa Xaa Xaa Xaa Xaa Xaa Xaa Xaa Xaa Xaa Xaa Xaa Xaa
                485                 490                 495

Thr Leu Asn Lys Leu Lys Gly Leu Val Ser Gln Leu Arg Pro Asp Val
            500                 505                 510

Ala Gln Ser Thr Ser Thr Thr Ser Asp Leu Ala Glu Tyr His Met Tyr
        515                 520                 525

Ile Asn Tyr Asp Tyr Leu Arg Ser Phe Thr Asp Glu Glu Ala Asn Val
        530                 535                 540

Leu Asp Leu Leu Leu Trp Trp Lys Gly Gln Arg Arg Gln Leu Pro Val
545                 550                 555                 560

Met Ser Ala Met Ala Gln Asp Phe Leu Ser Ile Gln Val Ser Ser Val
                565                 570                 575

Ala Ser Glu Arg Ala Phe Ser Ala Ser Lys Arg Val Leu Asp Glu Lys
            580                 585                 590

<210> SEQ ID NO 37
<211> LENGTH: 514
<212> TYPE: PRT
```

<213> ORGANISM: Antirrhinum majus

<400> SEQUENCE: 37

```
Lys Thr Lys Lys Ala Thr Val Trp Lys Trp Phe Ser Lys Val Thr Gly
  1               5                  10                  15

Ser Asn Trp Ala Gln Cys Leu Leu Cys Pro Thr Arg Tyr Ser His Lys
             20                  25                  30

Thr Gly Cys Gly Thr Gly Thr Leu Thr Arg His Leu Thr Ala Lys His
         35                  40                  45

Lys Asn Arg Asp Met Asp Ala Pro Asp Met Gln Arg Gln Pro Asp Gly
     50                  55                  60

Thr Met Ala Pro Trp Arg Tyr Asp Gln Asn Tyr Met Arg Ile Cys Leu
 65                  70                  75                  80

Ala Gln Phe Ile Val Gln Asn Glu Leu Pro Phe Ser Phe Ala Gln Asn
                 85                  90                  95

Glu Leu Phe Glu Asn Phe Leu Gln Lys Ala Val Gln Cys Lys Phe Lys
            100                 105                 110

Lys Ile Ser Arg Ala Thr Cys Phe Arg Asp Gly Val Lys Gln Tyr Glu
        115                 120                 125

Lys Glu Ile Ile Val Leu Arg Asn Glu Phe Lys Asn Phe Asn Gly Arg
    130                 135                 140

Ile Ser Leu Thr Ser Asp Leu Trp Gln Gly Ser Gly Ser Tyr His Phe
145                 150                 155                 160

Ser Cys Ile Thr Ala His Trp Ile Asp Lys Asp Trp Ile Met Arg Lys
                165                 170                 175

Arg Ile Ile Glu Phe Ala Gln Leu Asp Ser Pro His Asn Gly Asp Cys
            180                 185                 190

Ile Arg Asp Ala Thr Met Ser Ser Leu Asn Tyr Trp Gly Ile Lys Asp
        195                 200                 205

Lys Ile Met Ser Ile Ser Leu Asp Asn Ala Ser Asn Asn Val Asn Ala
    210                 215                 220

Ile Lys Ser Leu Lys Pro Ala Met Asn Leu Ile Leu Gly Gly Gln Leu
225                 230                 235                 240

Phe His Val Arg Cys Ile Cys His Ile Leu His Leu Cys Val Lys Asp
                245                 250                 255

Gly Leu Ser Val Leu Ile Gln Ser Ile Asp Arg Ile Arg Val Cys Leu
            260                 265                 270

Ser His Ile Asn Arg Tyr Pro Pro Arg Val Gln Ala Phe Asn Thr Val
        275                 280                 285

Cys Glu Thr His Gly Met Pro Ile Lys His Ile Tyr Leu Asp Val Pro
    290                 295                 300

His Arg Trp Asn Ala Thr Tyr Arg Met Leu Ile Glu Ala Lys Pro Tyr
305                 310                 315                 320

Ser Glu Pro Ile Thr Phe Phe Cys His Arg Ser Leu Gly Pro Asn Ser
                325                 330                 335

Ile Leu Ala Asp Asp Trp Asn Ile Cys Asp Ile Leu Val Pro Tyr Leu
            340                 345                 350

Val Tyr Phe Glu Glu Phe Thr Lys Ile Met Ser Ser Cys Tyr Thr Pro
        355                 360                 365

Thr Ser Asn Ile Met Leu Leu Tyr Met Val Ser Val Val Arg Leu Phe
    370                 375                 380

His Gln His Arg Asn His Ala Thr Leu Lys Asn Ile Ile Lys Glu Met
385                 390                 395                 400
```

```
Glu Lys Lys Trp Val Lys Tyr Tyr Lys Val Pro Asn Val Cys Ile
                405                 410                 415

Leu Ser Ser Cys Leu Asp Pro Arg Val Arg Leu Ile Gly Thr Leu Glu
            420                 425                 430

Leu Leu Glu Lys Tyr His Ser Ala Leu Asn Asn Val Tyr Asn Gly Asn
            435                 440                 445

Glu Glu Arg Asn Arg Ile Leu Gln Leu Leu Tyr Ser Leu Tyr Asp Met
        450                 455                 460

Tyr Ala Pro Ser Thr Asp Met Asp Glu Ser Pro Thr Asn Ala Ser Arg
465                 470                 475                 480

Gly Ser Gly Phe Ser Ile Phe Asp Glu Leu Leu Ser Asn Gln Gln Ser
                485                 490                 495

Asn Gln Pro Ser Val Gly Asn Tyr Thr Glu Ile His Leu Phe Val Gln
            500                 505                 510

Lys Pro
```

```
<210> SEQ ID NO 38
<211> LENGTH: 847
<212> TYPE: DNA
<213> ORGANISM: Dianthus caryophyllus

<400> SEQUENCE: 38
ccttgttttt gcaccttatg gacctaaatg gcgcatgctt aggaaaattt gttccttaca      60
catgttttct tctaaggctt tggacgattt tagacttgtc cgtcaggaag aagtatctat     120
actggtaaac gcgatagcaa aagcaggaac aaagccagta caactaggac aactactact     180
caacgtgtgc accacaaatg ccttatcgag ggtgatgcta gggaagcgag ttctcggtga     240
tggcacaggg aaaagcgacc caaaagccga ggaatttaag gacatggtgc tggagttaat     300
ggttctcacc ggagttttta acattggcga ttttgtaccg gcattggaat gtctagactt     360
acaaggtgtt gcatctaaaa tgaagaaatt acataaaaga cttgataatt ttatgagtaa     420
cattttggag gaacacaaga gtgttgcaca tcaacaaaat ggtggagatt tgctaagcac     480
tttgatatct ttgaaggata attgtgatgg tgaaggtggc aagtttagtg acacagaaat     540
taaggccttg ctattggatt tatttacagc tggaacagac acatcatcta gtacaactga     600
atgggccata gccgaactaa ttcgccatcc aaaaatctta gcccaagttc aacagaaat      660 ggactcagtc gtgggccgag accgactcat agccgaagct gacataccga acctaaccta     720
cttccaagcc gtaatcaaag aggttttccg acttcacccg tccacccgc tttccctacc      780 acgggtcgca aacgaatcgt gtgaaataaa cgggtaccac attcccaaaa acaccacttt     840
attggtg                                                                847
```

```
<210> SEQ ID NO 39
<211> LENGTH: 844
<212> TYPE: DNA
<213> ORGANISM: Dianthus caryophyllus

<400> SEQUENCE: 39
ccttgttttt gcaccttatg gacctaaatg gcgcatgctt aggaaaattt gttccttaca      60
catgttttct tctaaggctt tggacgattt tagacttgtc cgtcaggaag aagtatctat     120
actggtaaat gcgatagcaa aagcaggaac aaagccagta caactaggac aactactcaa     180
cgtgtgcacc acaaatgcct tatcgagggt gatgctaggg aagcgagttc tcggtgatgg     240
cacagggaaa agcgacccaa aagccgagga atttaaggac atggtgctgg agttaatggt     300
```

```
tctcaccgga gtttttaaca ttggcgattt tgtaccggca ttggaatgtc tagacttaca    360
aggtgttgca tctaaaatga agaaattaca taaaagactt gataatttta tgagtaacat    420
tttggaggaa cacaagagtg ttgcacatca acaaaatggt ggagatttgc taagcatttt    480
gatatctttg aaggataatt gtgatggtga aggtggcaag tttagtgcca cagaaattaa    540
ggccttgcta ttggatttat ttacagctgg aacagacaca tcatctagta caactgaatg    600
ggccatagcc gaactaattc gccatccaaa aatcttagcc caagttcaac aagaaatgga    660
ctcagtcgtg ggccgagacc gactcatagc cgaagctgac ataccgaacc taacctactt    720
ccaagccgta atcaaagagg ttttccgact tcacccgtcc accccgcttt ccctaccacg    780
ggtcgcaaac gaatcgtgcg aaataaacgg gtaccacatt cccaaaaaca ccactttatt    840
ggta                                                                 844
```